US011253179B2

(12) United States Patent
Bernstein et al.

(10) Patent No.: US 11,253,179 B2
(45) Date of Patent: Feb. 22, 2022

(54) SYSTEMS AND METHODS FOR COLLECTION AND/OR MANIPULATION OF BLOOD SPOTS OR OTHER BODILY FLUIDS

(71) Applicant: YourBio Health, Inc., Medford, MA (US)

(72) Inventors: Howard Bernstein, Cambridge, MA (US); Donald E. Chickering, III, Framingham, MA (US); Shawn Davis, Santa Monica, CA (US); Ping Gong, Belmont, MA (US); Kristin Horton, Brighton, MA (US); Scott James, Epping, NH (US)

(73) Assignee: YourBio Health, Inc., Medford, MA (US)

( * ) Notice: Subject to any disclaimer, the term of this patent is extended or adjusted under 35 U.S.C. 154(b) by 0 days.

(21) Appl. No.: 15/156,386

(22) Filed: May 17, 2016

(65) Prior Publication Data
US 2017/0127991 A1   May 11, 2017

Related U.S. Application Data

(63) Continuation of application No. 13/456,546, filed on Apr. 26, 2012, now abandoned.
(Continued)

(51) Int. Cl.
*A61B 5/15* (2006.01)
*A61M 1/34* (2006.01)
(Continued)

(52) U.S. Cl.
CPC ...... *A61B 5/150099* (2013.01); *A61B 5/1411* (2013.01); *A61B 5/1438* (2013.01);
(Continued)

(58) Field of Classification Search
CPC ............. A61B 5/14514; A61B 5/1411; A61B 5/150213; A61B 5/150099; A61B 5/1438;
(Continued)

(56) References Cited

U.S. PATENT DOCUMENTS 2,735,671 A    2/1956   Kuhn
2,961,233 A   11/1960   Ullrich
(Continued)

FOREIGN PATENT DOCUMENTS

CN    2065878 U    11/1990
CN    1222334 A     7/1999
(Continued)

OTHER PUBLICATIONS

Invitation to Pay Additional Fees dated Aug. 17, 2012 in connection with PCT/US2012/035173.
(Continued)

*Primary Examiner* — Patrick Fernandes
(74) *Attorney, Agent, or Firm* — Wolf, Greenfield & Sacks, P.C.

(57) ABSTRACT

The present invention generally relates to systems and methods for receiving blood (or other bodily fluids) from a subject, e.g., from or beneath the skin of a subject. In some cases, the blood (or other bodily fluids) may be deposited on a membrane or other substrate. For example, blood may be absorbed in a substrate, and dried in some cases to produce a dried blood spot. In one aspect, the present invention is generally directed to devices and methods for receiving blood from a subject, e.g., from the skin, using devices including a substance transfer component (which may contain, for example, one or more microneedles), and directing the blood on a substrate, e.g., for absorbing blood. The substrate, in some embodiments, may comprise filter paper or cotton-based paper. After absorption of some blood onto
(Continued)

the substrate, the substrate may be removed from the device and shipped or analyzed. In some cases, the device itself may be shipped or analyzed. For example, in some embodiments, a portion of the device may be sealed such that the substrate is contained within an airtight portion of the device, optionally containing desiccant. Other aspects are generally directed at other devices for receiving blood (or other bodily fluids), kits involving such devices, methods of making such devices, methods of using such devices, and the like.

25 Claims, 8 Drawing Sheets

Related U.S. Application Data

(60) Provisional application No. 61/549,437, filed on Oct. 20, 2011, provisional application No. 61/480,941, filed on Apr. 29, 2011.

(51) Int. Cl.

| | | |
|---|---|---|
| *A61M 1/36* | (2006.01) | |
| *A61B 5/145* | (2006.01) | |
| *A61B 5/151* | (2006.01) | |
| *A61B 5/154* | (2006.01) | |
| *B01L 3/00* | (2006.01) | |
| *G01N 33/18* | (2006.01) | |
| *A61B 5/1455* | (2006.01) | |
| *A61B 5/1486* | (2006.01) | |
| *A61B 10/00* | (2006.01) | |

(52) U.S. Cl.
CPC ...... *A61B 5/14514* (2013.01); *A61B 5/14532* (2013.01); *A61B 5/14539* (2013.01); *A61B 5/14546* (2013.01); *A61B 5/151* (2013.01); *A61B 5/154* (2013.01); *A61B 5/150022* (2013.01); *A61B 5/15105* (2013.01); *A61B 5/15142* (2013.01); *A61B 5/150213* (2013.01); *A61B 5/150221* (2013.01); *A61B 5/150229* (2013.01); *A61B 5/150343* (2013.01); *A61B 5/150358* (2013.01); *A61B 5/150412* (2013.01); *A61B 5/150419* (2013.01); *A61B 5/150503* (2013.01); *A61B 5/150755* (2013.01); *A61B 5/150969* (2013.01); *A61B 5/150984* (2013.01); *A61M 1/34* (2013.01); *A61M 1/3486* (2014.02); *A61M 1/3687* (2013.01); *B01L 3/502753* (2013.01); *G01N 33/1826* (2013.01); *A61B 5/1455* (2013.01); *A61B 5/1486* (2013.01); *A61B 10/0045* (2013.01); *A61B 2562/0295* (2013.01); *A61M 2202/0415* (2013.01); *A61M 2205/3334* (2013.01); *B01L 2300/0672* (2013.01); *B01L 2300/0681* (2013.01); *B01L 2300/087* (2013.01); *B01L 2300/0816* (2013.01); *B01L 2300/0874* (2013.01); *B01L 2400/049* (2013.01); *B01L 2400/0655* (2013.01); *B01L 2400/0688* (2013.01); *G01N 33/18* (2013.01)

(58) Field of Classification Search
CPC ............ A61B 5/14532; A61B 5/14539; A61B 5/14546; A61B 5/150022; A61B 5/150221; A61B 5/150229; A61B 5/150343; A61B 5/150358; A61B 5/150412; A61B 5/150419; A61B 5/150503; A61B 5/150755; A61B 5/150969; A61B 5/150984; A61B 5/151; A61B 5/15105; A61B 5/15142; A61B 5/154; A61B 5/1455; A61B 5/1486; A61B 10/0045; A61B 2562/0295; A61M 1/3486; A61M 1/34; A61M 1/3687; A61M 2202/0415; A61M 2205/3334; B01L 2300/0672; B01L 3/502753; B01L 2300/0681; B01L 2300/0816; B01L 2300/087; B01L 2300/0874; B01L 2400/049; B01L 2400/0655; B01L 2400/0688; G01N 33/18; G01N 33/1826

See application file for complete search history.

(56) References Cited

U.S. PATENT DOCUMENTS

| | | | |
|---|---|---|---|
| 2,976,735 | A | 3/1961 | Witte |
| 3,060,429 | A | 10/1962 | Winston |
| 3,072,122 | A | 1/1963 | Rosenthall |
| 3,339,546 | A | 9/1967 | Chen |
| 3,519,171 | A | 7/1970 | Kinnavy |
| 3,551,554 | A | 12/1970 | Herschler |
| 3,601,861 | A | 8/1971 | Moriwaki |
| 3,645,253 | A * | 2/1972 | Goverde ......... A61B 5/150251 600/578 |
| 3,711,602 | A | 1/1973 | Herschler |
| 3,711,606 | A | 1/1973 | Herschler |
| 3,740,421 | A | 6/1973 | Schmolka |
| 3,753,432 | A | 8/1973 | Guerra |
| 3,761,013 | A | 9/1973 | Schuster |
| 3,908,657 | A | 9/1975 | Kowarski |
| 3,964,482 | A | 6/1976 | Gerstel et al. |
| 4,103,684 | A | 8/1978 | Ismach |
| 4,150,744 | A | 4/1979 | Fennimore |
| 4,203,520 | A | 5/1980 | Schuster |
| 4,253,460 | A | 3/1981 | Chen et al. |
| 4,280,509 | A | 7/1981 | Bethkenhagen et al. |
| 4,329,999 | A | 5/1982 | Phillips |
| 4,437,567 | A | 3/1984 | Jeng |
| 4,537,776 | A | 8/1985 | Cooper |
| 4,553,552 | A | 11/1985 | Valdespino et al. |
| 4,557,943 | A | 12/1985 | Rosler et al. |
| 4,615,697 | A | 10/1986 | Robinson |
| 4,621,268 | A | 11/1986 | Keeling et al. |
| 4,637,403 | A | 1/1987 | Garcia et al. |
| 4,696,309 | A | 9/1987 | Stephan |
| 4,706,676 | A | 11/1987 | Peck |
| 4,740,365 | A | 4/1988 | Yukimatsu et al. |
| 4,756,314 | A | 7/1988 | Eckenhoff et al. |
| 4,764,378 | A | 8/1988 | Keith et al. |
| 4,772,470 | A | 9/1988 | Inoue et al. |
| 4,796,644 | A | 1/1989 | Polaschegg |
| 4,820,720 | A | 4/1989 | Sanders et al. |
| 4,821,733 | A | 4/1989 | Peck |
| 4,855,298 | A | 8/1989 | Yamada et al. |
| 4,855,989 | A | 8/1989 | Gyger |
| 4,856,533 | A | 8/1989 | Anraku et al. |
| 4,863,970 | A | 9/1989 | Patel et al. |
| 4,883,068 | A | 11/1989 | Dechow |
| 4,908,404 | A | 3/1990 | Benedict et al. |
| 4,957,108 | A | 9/1990 | Schoendorfer et al. |
| 4,971,068 | A | 11/1990 | Sahi |
| 4,973,468 | A | 11/1990 | Chiang et al. |
| 5,006,342 | A | 4/1991 | Cleary et al. |
| 5,014,718 | A * | 5/1991 | Mitchen ............ A61B 5/15142 600/584 |
| 5,015,677 | A | 5/1991 | Benedict et al. |
| 5,036,861 | A | 8/1991 | Sembrowich et al. |
| 5,054,499 | A | 10/1991 | Swierczek |
| 5,076,273 | A | 12/1991 | Schoendorfer et al. |
| 5,108,927 | A | 4/1992 | Dorn |
| 5,145,565 | A | 9/1992 | Kater et al. |
| 5,161,532 | A | 11/1992 | Joseph |
| 5,174,291 | A | 12/1992 | Schoonen et al. |
| 5,201,324 | A * | 4/1993 | Swierczek ......... A61B 5/15117 600/583 |
| 5,213,568 | A | 5/1993 | Lattin et al. |
| 5,231,993 | A | 8/1993 | Haber et al. |

(56) References Cited

U.S. PATENT DOCUMENTS

| | | | |
|---|---|---|---|
| 5,279,294 A | 1/1994 | Anderson et al. | |
| 5,320,607 A * | 6/1994 | Ishibashi | A61B 5/150022 |
| | | | 604/115 |
| 5,342,397 A | 8/1994 | Guido | |
| 5,379,895 A | 1/1995 | Foslien | |
| 5,402,798 A | 4/1995 | Swierczek et al. | |
| 5,438,984 A | 8/1995 | Schoendorfer | |
| 5,441,048 A | 8/1995 | Schoendorfer | |
| 5,441,490 A | 8/1995 | Svedman | |
| 5,443,080 A | 8/1995 | D'Angelo et al. | |
| 5,445,611 A | 8/1995 | Eppstein et al. | |
| 5,458,140 A | 10/1995 | Eppstein et al. | |
| 5,504,011 A | 4/1996 | Gavin et al. | |
| 5,505,212 A | 4/1996 | Keljmann et al. | |
| 5,507,288 A | 4/1996 | Bocker et al. | |
| 5,516,487 A * | 5/1996 | Rosenthal | G01N 33/521 |
| | | | 422/420 |
| 5,520,727 A | 5/1996 | Vreeland et al. | |
| 5,529,581 A | 6/1996 | Cusack | |
| 5,540,709 A | 7/1996 | Ramel | |
| 5,552,118 A | 9/1996 | Mayer | |
| 5,560,543 A | 10/1996 | Smith et al. | |
| 5,574,134 A | 11/1996 | Waite | |
| 5,580,794 A | 12/1996 | Allen | |
| 5,582,184 A | 12/1996 | Erickson et al. | |
| 5,591,403 A | 1/1997 | Gavin et al. | |
| 5,636,640 A | 6/1997 | Staehlin | |
| 5,638,815 A | 6/1997 | Schoendorfer | |
| 5,662,127 A | 9/1997 | De Vaughn | |
| 5,676,144 A | 10/1997 | Schoendorfer | |
| 5,680,872 A | 10/1997 | Sesekura et al. | |
| 5,682,233 A | 10/1997 | Brinda | |
| 5,685,875 A | 11/1997 | Hlavinka et al. | |
| 5,701,910 A | 12/1997 | Powles et al. | |
| 5,714,390 A | 2/1998 | Hallowitz et al. | |
| 5,741,138 A | 4/1998 | Rice et al. | |
| 5,746,217 A | 5/1998 | Erickson et al. | |
| 5,800,420 A | 9/1998 | Gross et al. | |
| 5,800,781 A | 9/1998 | Gavin et al. | |
| 5,807,375 A | 9/1998 | Gross et al. | |
| 5,811,108 A | 9/1998 | Goeringer | |
| 5,813,614 A | 9/1998 | Coffee | |
| 5,817,011 A | 10/1998 | Schoendorfer | |
| 5,817,012 A | 10/1998 | Schoendorfer | |
| 5,820,570 A | 10/1998 | Erickson et al. | |
| 5,820,622 A | 10/1998 | Gross et al. | |
| 5,823,973 A | 10/1998 | Racchini et al. | |
| 5,857,983 A | 1/1999 | Douglas et al. | |
| 5,858,188 A | 1/1999 | Soane et al. | |
| 5,873,900 A | 2/1999 | Maurer et al. | |
| 5,876,675 A | 3/1999 | Kennedy | |
| 5,879,310 A | 3/1999 | Sopp et al. | |
| 5,879,311 A | 3/1999 | Duchon et al. | |
| 5,879,367 A | 3/1999 | Latterell et al. | |
| 5,885,211 A | 3/1999 | Eppstein et al. | |
| 5,891,053 A | 4/1999 | Sesekura | |
| 5,897,508 A | 4/1999 | Konrad | |
| 5,944,662 A | 8/1999 | Schoendorfer | |
| 5,951,492 A | 9/1999 | Douglas et al. | |
| 5,951,493 A | 9/1999 | Douglas et al. | |
| 5,955,096 A | 9/1999 | Santos et al. | |
| 5,963,136 A | 10/1999 | O'Brien | |
| 5,964,718 A | 10/1999 | Duchon et al. | |
| 5,972,386 A | 10/1999 | Burgoyne | |
| 5,985,312 A | 11/1999 | Jacob et al. | |
| 5,998,588 A | 12/1999 | Hoffman et al. | |
| 6,007,845 A | 12/1999 | Domb et al. | |
| 6,015,392 A | 1/2000 | Douglas et al. | |
| 6,024,710 A | 2/2000 | Miller et al. | |
| 6,027,459 A | 2/2000 | Shain et al. | |
| 6,040,135 A * | 3/2000 | Tyrrell | A61B 10/0045 |
| | | | 422/50 |
| 6,044,303 A | 3/2000 | Agarwala et al. | |
| 6,048,337 A | 4/2000 | Svedman | |
| 6,050,988 A | 4/2000 | Zuck | |
| 6,063,029 A | 5/2000 | Saita et al. | |
| 6,063,039 A | 5/2000 | Cunningham et al. | |
| 6,063,365 A | 5/2000 | Shefer et al. | |
| 6,066,103 A | 5/2000 | Duchon et al. | |
| 6,071,249 A | 6/2000 | Cunningham et al. | |
| 6,071,250 A | 6/2000 | Douglas et al. | |
| 6,071,251 A | 6/2000 | Cunningham et al. | |
| 6,080,116 A | 6/2000 | Erickson et al. | |
| 6,083,196 A | 7/2000 | Trautman et al. | |
| 6,091,975 A | 7/2000 | Daddona et al. | |
| 6,093,156 A | 7/2000 | Cunningham et al. | |
| 6,099,484 A | 8/2000 | Douglas et al. | |
| 6,107,102 A | 8/2000 | Ferrari | |
| 6,126,899 A | 10/2000 | Woudenberg et al. | |
| 6,132,449 A | 10/2000 | Lum et al. | |
| 6,132,702 A | 10/2000 | Witt et al. | |
| 6,133,318 A | 10/2000 | Hart | |
| 6,152,889 A | 11/2000 | Sopp et al. | |
| 6,152,942 A | 11/2000 | Brenneman et al. | |
| 6,155,992 A | 12/2000 | Henning et al. | |
| 6,162,639 A | 12/2000 | Douglas | |
| 6,190,315 B1 | 2/2001 | Kost et al. | |
| 6,192,890 B1 | 2/2001 | Levy et al. | |
| 6,203,504 B1 | 3/2001 | Latterell et al. | |
| 6,206,841 B1 | 3/2001 | Cunningham et al. | |
| 6,219,574 B1 | 4/2001 | Cormier et al. | |
| 6,228,100 B1 | 5/2001 | Schraga | |
| 6,230,051 B1 | 5/2001 | Cormier et al. | |
| 6,234,990 B1 | 5/2001 | Rowe et al. | |
| 6,235,313 B1 | 5/2001 | Mathiowitz et al. | |
| 6,252,129 B1 | 6/2001 | Coffee | |
| 6,261,245 B1 * | 7/2001 | Kawai | A61B 5/15186 |
| | | | 600/576 |
| 6,267,724 B1 | 7/2001 | Taylor | |
| 6,283,926 B1 | 9/2001 | Cunningham et al. | |
| 6,306,104 B1 | 10/2001 | Cunningham et al. | |
| 6,306,993 B1 | 10/2001 | Rothbard et al. | |
| 6,309,887 B1 * | 10/2001 | Ray | G01N 33/721 |
| | | | 422/410 |
| 6,315,951 B1 | 11/2001 | Markart | |
| 6,319,210 B1 | 11/2001 | Douglas et al. | |
| 6,322,574 B1 | 11/2001 | Llyod | |
| 6,332,871 B1 | 12/2001 | Douglas et al. | |
| 6,334,856 B1 | 1/2002 | Allen et al. | |
| 6,340,354 B1 | 1/2002 | Rambin | |
| 6,349,229 B1 | 2/2002 | Watanabe et al. | |
| 6,349,850 B1 | 2/2002 | Cheikh | |
| 6,361,944 B1 | 3/2002 | Mirkin et al. | |
| 6,364,890 B1 | 4/2002 | Lum et al. | |
| 6,379,317 B1 | 4/2002 | Kintzig et al. | |
| 6,379,324 B1 | 4/2002 | Gartstein et al. | |
| 6,391,471 B1 | 5/2002 | Hiraoka et al. | |
| 6,394,952 B1 | 5/2002 | Anderson et al. | |
| 6,406,919 B1 | 6/2002 | Tyrrell | |
| 6,409,679 B2 | 6/2002 | Pyo | |
| 6,436,078 B1 | 8/2002 | Svedman | |
| 6,440,096 B1 | 8/2002 | Lastovich et al. | |
| 6,455,324 B1 | 9/2002 | Douglas | |
| 6,461,644 B1 | 10/2002 | Jackson et al. | |
| 6,464,649 B1 | 10/2002 | Duchon et al. | |
| 6,465,002 B1 | 10/2002 | Mathiowitz et al. | |
| 6,485,439 B1 | 11/2002 | Roe et al. | |
| 6,485,703 B1 | 11/2002 | Cote et al. | |
| 6,491,657 B2 | 12/2002 | Rowe et al. | |
| 6,491,902 B2 | 12/2002 | Shefer et al. | |
| 6,501,976 B1 | 12/2002 | Sohrab | |
| 6,502,697 B1 | 1/2003 | Crampton et al. | |
| 6,503,209 B2 | 1/2003 | Hakky et al. | |
| 6,503,231 B1 | 1/2003 | Prausnitz et al. | |
| 6,506,168 B1 | 1/2003 | Fathallah et al. | |
| 6,527,716 B1 | 3/2003 | Eppstein | |
| 6,532,386 B2 | 3/2003 | Sun et al. | |
| 6,537,243 B1 | 3/2003 | Henning et al. | |
| 6,537,264 B1 | 3/2003 | Cormier et al. | |
| 6,538,089 B1 | 3/2003 | Samra et al. | |
| 6,540,675 B2 | 4/2003 | Aceti et al. | |
| 6,548,264 B1 | 4/2003 | Tan et al. | |
| 6,558,361 B1 | 5/2003 | Yeshurun | |

(56) References Cited

U.S. PATENT DOCUMENTS

| | | |
|---|---|---|
| 6,562,014 B2 * | 5/2003 | Lin .................... A61B 5/14532 600/562 |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B1 | 9/2003 | Dillon et al. |
| 6,629,057 B2 | 9/2003 | Zweig et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,712,792 B2 | 3/2004 | Leong |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,896,666 B2 | 5/2005 | Kochamba |
| 6,899,851 B2 | 5/2005 | Allen et al. |
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,925,317 B1 | 8/2005 | Samuels et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,351 B2 | 11/2005 | Knoll |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,025,774 B2 | 4/2006 | Freeman et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,131,987 B2 | 11/2006 | Sherman et al. |
| 7,133,717 B2 | 11/2006 | Coston et al. |
| 7,137,957 B2 | 11/2006 | Erickson et al. |
| 7,150,755 B2 | 12/2006 | Levaughn et al. |
| 7,172,071 B2 | 2/2007 | Hawkins |
| 7,174,199 B2 | 2/2007 | Berner et al. |
| 7,182,910 B2 | 2/2007 | Allen et al. |
| 7,185,764 B2 | 3/2007 | Lee et al. |
| 7,235,056 B2 | 6/2007 | Duchon et al. |
| 7,247,144 B2 | 7/2007 | Douglas et al. |
| 7,264,627 B2 | 9/2007 | Perez |
| 7,316,671 B2 | 1/2008 | Lastovich et al. |
| 7,335,166 B2 | 2/2008 | Faupel et al. |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,422,567 B2 | 9/2008 | Lastovich et al. |
| 7,429,258 B2 | 9/2008 | Angel et al. |
| 7,537,590 B2 | 5/2009 | Santini et al. |
| 7,544,185 B2 | 6/2009 | Bengtsson |
| 7,556,615 B2 | 7/2009 | Pettis et al. |
| 7,572,237 B2 | 8/2009 | Saikley et al. |
| 7,575,717 B2 | 8/2009 | Cooke et al. |
| 7,585,278 B2 | 9/2009 | Aceti et al. |
| 7,585,412 B2 | 9/2009 | Gorsuch et al. |
| 7,631,760 B2 | 12/2009 | Guelzow et al. |
| 7,758,518 B2 | 7/2010 | Perez et al. |
| 7,767,017 B2 | 8/2010 | Lahann et al. |
| 7,811,236 B2 | 10/2010 | List et al. |
| 7,811,302 B2 | 10/2010 | Steg |
| 7,833,172 B2 | 11/2010 | Hein et al. |
| 7,883,473 B2 | 2/2011 | LeVaughn et al. |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,058,077 B2 | 11/2011 | Groll et al. |
| 8,071,384 B2 | 12/2011 | Burke et al. |
| 8,075,826 B2 | 12/2011 | Lastovich et al. |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,241,651 B2 | 8/2012 | Lahann |
| 8,246,582 B2 | 8/2012 | Angel et al. |
| 8,344,028 B2 | 1/2013 | Xu et al. |
| 8,383,044 B2 | 2/2013 | Davis et al. |
| 8,460,210 B2 | 6/2013 | Jacobs |
| 8,465,425 B2 | 6/2013 | Heller et al. |
| 8,517,938 B2 | 8/2013 | Eisenhardt et al. |
| 8,523,894 B2 | 9/2013 | Schmelzeisen-Redeker et al. |
| 8,530,231 B2 | 9/2013 | Nakae et al. |
| 8,561,795 B2 | 10/2013 | Schott |
| 8,628,724 B2 | 1/2014 | Kuenstner |
| 8,647,575 B2 | 2/2014 | Ohashi |
| 8,808,202 B2 | 8/2014 | Brancazio |
| 8,821,412 B2 | 9/2014 | Gonzalez-Zugasti et al. |
| 8,821,446 B2 | 9/2014 | Trautman et al. |
| 8,827,971 B2 | 9/2014 | Chickering, III et al. |
| 8,870,903 B2 | 10/2014 | LeVaughn et al. |
| 8,882,794 B2 | 11/2014 | Lum |
| 8,900,180 B2 | 12/2014 | Wolter et al. |
| 8,934,955 B2 | 1/2015 | Schraga |
| 8,971,980 B2 | 3/2015 | Mace et al. |
| 9,028,426 B2 | 5/2015 | List et al. |
| 9,033,898 B2 | 5/2015 | Chickering, III et al. |
| 9,033,989 B2 | 5/2015 | Wolfson et al. |
| 9,039,638 B2 | 5/2015 | Arnitz |
| 9,041,541 B2 | 5/2015 | Levinson et al. |
| 9,101,302 B2 | 8/2015 | Mace et al. |
| 9,113,836 B2 | 8/2015 | Bernstein et al. |
| 9,119,578 B2 | 9/2015 | Haghgooie et al. |
| 9,295,417 B2 | 3/2016 | Haghgooie et al. |
| 9,730,624 B2 | 8/2017 | Gonzalez-Zugasti et al. |
| 9,775,551 B2 | 10/2017 | Bernstein et al. |
| 10,188,335 B2 | 1/2019 | Haghgooie et al. |
| 10,543,310 B2 | 1/2020 | Bernstein et al. |
| 10,799,166 B2 | 10/2020 | Gonzalez-Zugasti et al. |
| 10,835,163 B2 | 11/2020 | Haghgooie et al. |

(56) References Cited

U.S. PATENT DOCUMENTS

| | | |
|---|---|---|
| 10,939,860 B2 | 3/2021 | Levinson et al. |
| 2001/0005772 A1 | 6/2001 | Kisakibaru |
| 2002/0010414 A1 | 1/2002 | Coston et al. |
| 2002/0013538 A1 | 1/2002 | Teller |
| 2002/0065453 A1 | 5/2002 | Lesho et al. |
| 2002/0076443 A1 | 6/2002 | Stein et al. |
| 2002/0077584 A1 | 6/2002 | Lin et al. |
| 2002/0082543 A1 | 6/2002 | Park et al. |
| 2002/0087056 A1 | 7/2002 | Aceti et al. |
| 2002/0099308 A1 | 7/2002 | Bojan et al. |
| 2002/0099356 A1 | 7/2002 | Unger et al. |
| 2002/0112981 A1 | 8/2002 | Cooper et al. |
| 2002/0115967 A1 | 8/2002 | Svedman |
| 2002/0119136 A1 | 8/2002 | Johansen |
| 2002/0130042 A1 | 9/2002 | Moerman et al. |
| 2002/0130093 A1 | 9/2002 | Ferrara et al. |
| 2002/0138049 A1 | 9/2002 | Allen |
| 2002/0143320 A1 | 10/2002 | Levin |
| 2002/0168290 A1 | 11/2002 | Yuzhakov et al. |
| 2002/0169393 A1 | 11/2002 | Cunningham et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0187556 A1 | 12/2002 | Shartle et al. |
| 2002/0188221 A1 | 12/2002 | Sohrab |
| 2003/0004437 A1 | 1/2003 | Collins et al. |
| 2003/0040682 A1 | 2/2003 | Tapper |
| 2003/0055326 A1 | 3/2003 | Sohrab |
| 2003/0065294 A1 | 4/2003 | Pickup et al. |
| 2003/0083618 A1 | 5/2003 | Angel et al. |
| 2003/0083645 A1 | 5/2003 | Angel et al. |
| 2003/0083685 A1 | 5/2003 | Freeman et al. |
| 2003/0083686 A1 | 5/2003 | Freeman et al. |
| 2003/0100846 A1 | 5/2003 | Custer et al. |
| 2003/0109807 A1 | 6/2003 | Knoll |
| 2003/0113540 A1 | 6/2003 | Anderson et al. |
| 2003/0135158 A1 | 7/2003 | Gonnelli |
| 2003/0135167 A1 | 7/2003 | Gonnelli |
| 2003/0135201 A1 | 7/2003 | Gonnelli |
| 2003/0135333 A1 | 7/2003 | Aceti et al. |
| 2003/0143746 A1 | 7/2003 | Sage |
| 2003/0159615 A1 | 8/2003 | Anderson et al. |
| 2003/0162304 A1* | 8/2003 | Dority .................. B01L 3/502 436/180 |
| 2003/0181863 A1 | 9/2003 | Ackley et al. |
| 2003/0187394 A1 | 10/2003 | Wilkinson et al. |
| 2003/0187395 A1 | 10/2003 | Gabel et al. |
| 2003/0195398 A1 | 10/2003 | Suzuki et al. |
| 2003/0204148 A1 | 10/2003 | Lange et al. |
| 2003/0208138 A1 | 11/2003 | Olson |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0053894 A1 | 3/2004 | Mazess et al. |
| 2004/0058458 A1 | 3/2004 | Anker et al. |
| 2004/0087990 A1 | 5/2004 | Boecker et al. |
| 2004/0096959 A1 | 5/2004 | Stiene et al. |
| 2004/0098009 A1 | 5/2004 | Boecker et al. |
| 2004/0102717 A1 | 5/2004 | Qi |
| 2004/0106904 A1 | 6/2004 | Gonnelli et al. |
| 2004/0133126 A1 | 7/2004 | McNenny |
| 2004/0137640 A1* | 7/2004 | Hirao .................. B01L 3/5023 436/514 |
| 2004/0138688 A1 | 7/2004 | Giraud |
| 2004/0162521 A1 | 8/2004 | Bengtsson |
| 2004/0163987 A1 | 8/2004 | Allen |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0000514 A1 | 1/2005 | Sullivan et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0033197 A1 | 2/2005 | Cottler |
| 2005/0038669 A1 | 2/2005 | Sachdeva et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |
| 2005/0090766 A1 | 4/2005 | Montanari |
| 2005/0106066 A1 | 5/2005 | Saltsman et al. |
| 2005/0106713 A1 | 5/2005 | Phan et al. |
| 2005/0137481 A1 | 6/2005 | Sheard et al. |
| 2005/0137531 A1 | 6/2005 | Prausnitz et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1 | 9/2005 | Brauker et al. |
| 2005/0215923 A1 | 9/2005 | Wiegel |
| 2005/0221276 A1 | 10/2005 | Rozakis et al. |
| 2005/0227269 A1 | 10/2005 | Lloyd, Jr. et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2005/0267422 A1 | 12/2005 | Kriesel |
| 2006/0001551 A1 | 1/2006 | Kraft et al. |
| 2006/0004271 A1 | 1/2006 | Peyser et al. |
| 2006/0004303 A1 | 1/2006 | Weidenhaupt et al. |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0089566 A1 | 4/2006 | DeHart |
| 2006/0091669 A1 | 5/2006 | Wilkinson |
| 2006/0100654 A1 | 5/2006 | Fukuda et al. |
| 2006/0129065 A1 | 6/2006 | Matsumoto et al. |
| 2006/0142651 A1 | 6/2006 | Brister et al. |
| 2006/0157362 A1 | 7/2006 | Schraga |
| 2006/0189895 A1 | 8/2006 | Neel et al. |
| 2006/0200046 A1 | 9/2006 | Windus-Smith et al. |
| 2006/0202385 A1 | 9/2006 | Xu et al. |
| 2006/0228259 A1 | 10/2006 | Samsoondar |
| 2006/0257883 A1 | 11/2006 | Bjorkaker et al. |
| 2006/0258959 A1 | 11/2006 | Sode |
| 2006/0259195 A1 | 11/2006 | Eliuk et al. |
| 2006/0264779 A1 | 11/2006 | Kemp et al. |
| 2006/0264782 A1 | 11/2006 | Holmes et al. |
| 2007/0004989 A1 | 1/2007 | Dhillon |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0031293 A1 | 2/2007 | Beatty |
| 2007/0036686 A1* | 2/2007 | Hatamian ............ B01L 3/5021 422/400 |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0083131 A1 | 4/2007 | Escutia et al. |
| 2007/0088248 A1 | 4/2007 | Glenn et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161926 A1 | 7/2007 | Imamura et al. |
| 2007/0161964 A1 | 7/2007 | Yukhazov |
| 2007/0167340 A1 | 7/2007 | Barthel et al. |
| 2007/0169411 A1 | 7/2007 | Thiessen et al. |

(56) References Cited

U.S. PATENT DOCUMENTS

| | | | |
|---|---|---|---|
| 2007/0173740 A1* | 7/2007 | Chan | A61B 5/15146 600/583 |
| 2007/0179404 A1 | 8/2007 | Escutia et al. | |
| 2007/0185432 A1 | 8/2007 | Etheredge et al. | |
| 2007/0185515 A1 | 8/2007 | Stout | |
| 2007/0208275 A1 | 9/2007 | Vinogradov et al. | |
| 2007/0213638 A1* | 9/2007 | Herbrechtsmeier | A61B 5/15186 600/583 |
| 2007/0225676 A1 | 9/2007 | Prausnitz et al. | |
| 2007/0231355 A1 | 10/2007 | Quadir et al. | |
| 2007/0232956 A1 | 10/2007 | Harman et al. | |
| 2007/0233199 A1 | 10/2007 | Moore et al. | |
| 2007/0237800 A1 | 10/2007 | Lahann | |
| 2007/0238943 A1 | 10/2007 | Poulsen et al. | |
| 2007/0249962 A1 | 10/2007 | Alden et al. | |
| 2007/0270672 A1 | 11/2007 | Hayter | |
| 2007/0272738 A1 | 11/2007 | Berkun | |
| 2007/0275193 A1* | 11/2007 | DeSimone | B01L 3/502707 428/34.1 |
| 2008/0009763 A1 | 1/2008 | Chiou et al. | |
| 2008/0014627 A1 | 1/2008 | Merchant et al. | |
| 2008/0021491 A1 | 1/2008 | Freeman et al. | |
| 2008/0033319 A1 | 2/2008 | Kloepfer et al. | |
| 2008/0051689 A1* | 2/2008 | Gura | A61M 1/16 604/6.07 |
| 2008/0077096 A1 | 3/2008 | Nakamura et al. | |
| 2008/0077430 A1 | 3/2008 | Singer et al. | |
| 2008/0081695 A1 | 4/2008 | Patchen | |
| 2008/0086051 A1 | 4/2008 | Voegele | |
| 2008/0099478 A1 | 5/2008 | Gleich | |
| 2008/0103434 A1 | 5/2008 | Lastovich et al. | |
| 2008/0108958 A1 | 5/2008 | Carter et al. | |
| 2008/0108959 A1 | 5/2008 | Jung et al. | |
| 2008/0112886 A1 | 5/2008 | Mitragotri et al. | |
| 2008/0125673 A1 | 5/2008 | Carano et al. | |
| 2008/0125743 A1 | 5/2008 | Yuzhakov | |
| 2008/0129486 A1 | 6/2008 | Jeckelmann et al. | |
| 2008/0140049 A1 | 6/2008 | Kirby | |
| 2008/0154107 A1 | 6/2008 | Jina | |
| 2008/0167535 A1 | 7/2008 | Stivoric et al. | |
| 2008/0167613 A1 | 7/2008 | Khouri et al. | |
| 2008/0183140 A1 | 7/2008 | Paproski et al. | |
| 2008/0183144 A1 | 7/2008 | Trautman et al. | |
| 2008/0199851 A1 | 8/2008 | Egan et al. | |
| 2008/0200791 A1 | 8/2008 | Simpson et al. | |
| 2008/0200838 A1 | 8/2008 | Goldberger et al. | |
| 2008/0217391 A1 | 9/2008 | Roof et al. | |
| 2008/0220411 A1 | 9/2008 | McNaughton et al. | |
| 2008/0221407 A1 | 9/2008 | Baker | |
| 2008/0267537 A1 | 10/2008 | Thuries | |
| 2008/0269666 A1 | 10/2008 | Wang et al. | |
| 2008/0275327 A1 | 11/2008 | Faarbaek et al. | |
| 2008/0275378 A1 | 11/2008 | Herndon | |
| 2008/0281290 A1 | 11/2008 | Yodfat et al. | |
| 2008/0283603 A1 | 11/2008 | Barron et al. | |
| 2008/0300508 A1 | 12/2008 | Tomer | |
| 2008/0315994 A1 | 12/2008 | Maltseff et al. | |
| 2008/0319347 A1 | 12/2008 | Keren | |
| 2009/0036795 A1 | 2/2009 | Duineveld et al. | |
| 2009/0043250 A1 | 2/2009 | Gonnelli | |
| 2009/0048536 A1 | 2/2009 | Freeman et al. | |
| 2009/0054813 A1 | 2/2009 | Freeman et al. | |
| 2009/0054971 A1 | 2/2009 | Mitsunaga et al. | |
| 2009/0076453 A1 | 3/2009 | Mejlhede et al. | |
| 2009/0088648 A1 | 4/2009 | Jaffe et al. | |
| 2009/0099427 A1 | 4/2009 | Jina et al. | |
| 2009/0099478 A1 | 4/2009 | Cassells et al. | |
| 2009/0099529 A1 | 4/2009 | Anderson et al. | |
| 2009/0101447 A1 | 4/2009 | Durham et al. | |
| 2009/0105614 A1 | 4/2009 | Momose et al. | |
| 2009/0118662 A1 | 5/2009 | Schnall | |
| 2009/0124994 A1 | 5/2009 | Roe | |
| 2009/0130646 A1 | 5/2009 | Fletcher et al. | |
| 2009/0131829 A1 | 5/2009 | Freeman et al. | |
| 2009/0155838 A1 | 6/2009 | Hale | |
| 2009/0182306 A1 | 7/2009 | Lee et al. | |
| 2009/0187117 A1 | 7/2009 | Imai | |
| 2009/0187160 A1 | 7/2009 | McAllister et al. | |
| 2009/0187167 A1 | 7/2009 | Sexton et al. | |
| 2009/0198189 A1 | 8/2009 | Simons et al. | |
| 2009/0198215 A1 | 8/2009 | Chong et al. | |
| 2009/0206158 A1 | 8/2009 | Thuries et al. | |
| 2009/0209883 A1 | 8/2009 | Higgins et al. | |
| 2009/0215159 A1 | 8/2009 | Kirby | |
| 2009/0216103 A1 | 8/2009 | Brister et al. | |
| 2009/0216629 A1 | 8/2009 | James et al. | |
| 2009/0264720 A1 | 10/2009 | Torjman et al. | |
| 2009/0270792 A1 | 10/2009 | Lastovich et al. | |
| 2009/0315684 A1 | 12/2009 | Sacco et al. | |
| 2009/0318779 A1 | 12/2009 | Tran | |
| 2009/0318846 A1 | 12/2009 | Prausnitz et al. | |
| 2010/0010374 A1 | 1/2010 | Escutia et al. | |
| 2010/0021947 A1 | 1/2010 | Emery et al. | |
| 2010/0030111 A1 | 2/2010 | Perriere | |
| 2010/0042137 A1 | 2/2010 | Oronsky et al. | |
| 2010/0049126 A1 | 2/2010 | Bronfeld et al. | |
| 2010/0069726 A1 | 3/2010 | Levinson | |
| 2010/0069730 A1 | 3/2010 | Bergstrom et al. | |
| 2010/0094170 A1 | 4/2010 | Wilson et al. | |
| 2010/0111970 A1 | 5/2010 | Pons et al. | |
| 2010/0114014 A1 | 5/2010 | Roser | |
| 2010/0121368 A1 | 5/2010 | Kim et al. | |
| 2010/0147763 A1 | 6/2010 | Tsou et al. | |
| 2010/0160894 A1 | 6/2010 | Julian et al. | |
| 2010/0210970 A1 | 8/2010 | Horikawa et al. | |
| 2010/0222703 A1 | 9/2010 | Takashima et al. | |
| 2010/0234768 A1 | 9/2010 | Uchiyama et al. | |
| 2010/0240079 A1 | 9/2010 | Jackson | |
| 2010/0249560 A1 | 9/2010 | Levinson et al. | |
| 2010/0256465 A1 | 10/2010 | Bernstein et al. | |
| 2010/0256524 A1 | 10/2010 | Levinson et al. | |
| 2010/0261988 A1 | 10/2010 | Tamir | |
| 2010/0269837 A1 | 10/2010 | Levinson et al. | |
| 2010/0272652 A1 | 10/2010 | Levinson et al. | |
| 2010/0282834 A1 | 11/2010 | Devergne | |
| 2010/0292191 A1 | 11/2010 | Mainx et al. | |
| 2010/0318111 A1 | 12/2010 | Sarna et al. | |
| 2010/0324449 A1 | 12/2010 | Rostaing et al. | |
| 2010/0324451 A1 | 12/2010 | Ishibashi et al. | |
| 2011/0003770 A1 | 1/2011 | Eek | |
| 2011/0009847 A1 | 1/2011 | Levinson et al. | |
| 2011/0034830 A1 | 2/2011 | Nakamura et al. | |
| 2011/0040208 A1 | 2/2011 | Mcminn et al. | |
| 2011/0040317 A1 | 2/2011 | Lee et al. | |
| 2011/0105828 A1 | 5/2011 | Perless et al. | |
| 2011/0105872 A1 | 5/2011 | Chickering et al. | |
| 2011/0105951 A1 | 5/2011 | Bernstein et al. | |
| 2011/0105952 A1 | 5/2011 | Bernstein et al. | |
| 2011/0112384 A1 | 5/2011 | Eisenhardt et al. | |
| 2011/0112438 A1 | 5/2011 | Radzuinas et al. | |
| 2011/0125058 A1 | 5/2011 | Levinson et al. | |
| 2011/0137203 A1 | 6/2011 | Nishiuchi et al. | |
| 2011/0172508 A1 | 7/2011 | Chickering, III et al. | |
| 2011/0172510 A1 | 7/2011 | Chickering, III et al. | |
| 2011/0181410 A1 | 7/2011 | Levinson et al. | |
| 2011/0212453 A1 | 9/2011 | Agarwal et al. | |
| 2011/0245708 A1 | 10/2011 | Finkel et al. | |
| 2011/0251562 A1 | 10/2011 | Chickering, III et al. | |
| 2011/0276027 A1 | 11/2011 | Trautman et al. | |
| 2011/0281346 A1 | 11/2011 | Halpern et al. | |
| 2011/0282173 A1 | 11/2011 | Fonduca et al. | |
| 2011/0288389 A9 | 11/2011 | Levinson et al. | |
| 2011/0306853 A1 | 12/2011 | Black et al. | |
| 2012/0010529 A1 | 1/2012 | Chickering, III et al. | |
| 2012/0016308 A1 | 1/2012 | Schott | |
| 2012/0039809 A1 | 2/2012 | Levinson et al. | |
| 2012/0041338 A1 | 2/2012 | Chickering et al. | |
| 2012/0089050 A1 | 4/2012 | Fukuda | |
| 2012/0123297 A1 | 5/2012 | Brancazio | |
| 2012/0184906 A1 | 7/2012 | McAllister | |
| 2012/0271125 A1 | 10/2012 | Bernstein et al. | |
| 2012/0275955 A1 | 11/2012 | Haghgooie et al. | |

(56) References Cited

U.S. PATENT DOCUMENTS

| | | | |
|---|---|---|---|
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0131741 A1 | 5/2013 | Kourtis et al. |
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |
| 2015/0157787 A1 | 6/2015 | Cully et al. |
| 2015/0278476 A1 | 10/2015 | Levinson et al. |
| 2015/0313522 A1 | 11/2015 | Bernstein et al. |
| 2015/0320349 A1 | 11/2015 | Haghgooie et al. |
| 2015/0342509 A1 | 12/2015 | Peeters et al. |
| 2016/0038068 A1 | 2/2016 | Chickering et al. |
| 2016/0262676 A1 | 9/2016 | Haghgooie et al. |
| 2017/0067803 A1 | 3/2017 | Jackson et al. |
| 2017/0120022 A1 | 5/2017 | Chickering et al. |
| 2017/0120023 A1 | 5/2017 | Davis et al. |
| 2017/0127990 A1 | 5/2017 | Levinson et al. |
| 2017/0127991 A1 | 5/2017 | Bernstein et al. |
| 2017/0172481 A1 | 6/2017 | Berthier et al. |
| 2017/0215790 A1 | 8/2017 | Levinson et al. |
| 2017/0224264 A1 | 8/2017 | Brancazio |
| 2017/0281852 A1 | 10/2017 | Bernstein et al. |
| 2018/0008183 A1 | 1/2018 | Chickering et al. |
| 2018/0132774 A1 | 5/2018 | Gonzalez-Zugasti et al. |
| 2018/0242890 A1 | 8/2018 | Chickering et al. |
| 2018/0310884 A1 | 11/2018 | Chickering et al. |
| 2018/0317829 A9 | 11/2018 | Gonzalez-Zugasti et al. |
| 2019/0023473 A1 | 1/2019 | Schott |
| 2019/0053740 A1 | 2/2019 | Davis et al. |
| 2019/0159709 A1 | 5/2019 | Barone et al. |
| 2019/0209820 A1 | 7/2019 | Chickering et al. |
| 2019/0216380 A1 | 7/2019 | Ivosevic et al. |
| 2019/0336058 A1 | 11/2019 | Haghgooie et al. |
| 2020/0015751 A9 | 1/2020 | Chickering et al. |
| 2020/0353155 A1 | 11/2020 | Bernstein et al. |
| 2021/0022681 A1 | 1/2021 | Chickering et al. |
| 2021/0228124 A1 | 7/2021 | Gonzalez-Zugasti et al. |

FOREIGN PATENT DOCUMENTS

| | | |
|---|---|---|
| CN | 2331315 Y | 8/1999 |
| CN | 2462854 Y | 12/2001 |
| CN | 2600055 Y | 1/2004 |
| CN | 1499949 A | 5/2004 |
| CN | 1501788 A | 6/2004 |
| CN | 1524493 A | 9/2004 |
| CN | 1551743 A | 12/2004 |
| CN | 1753646 A | 3/2006 |
| CN | 101248998 A | 8/2008 |
| CN | 101347384 A | 1/2009 |
| CN | 101678196 A | 3/2010 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 535 266 A1 | 4/1993 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 027 864 A1 | 8/2000 |
| EP | 1 360 934 A1 | 11/2003 |
| EP | 1 437 093 A1 | 7/2004 |
| EP | 1437093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1 639 938 A1 | 3/2006 |
| EP | 1 652 551 A2 | 5/2006 |
| EP | 1 834 589 A2 | 9/2007 |
| EP | 1 844 710 B1 | 10/2007 |
| EP | 1844710 A1 | 10/2007 |
| EP | 1 997 431 A1 | 12/2008 |
| EP | 2 064 993 A1 | 6/2009 |
| EP | 2 077 128 A1 | 7/2009 |
| EP | 1 187 653 B1 | 3/2010 |
| EP | 2 701 601 A1 | 3/2014 |
| EP | 3087919 A1 | 11/2016 |
| FR | 2929135 A1 | 10/2009 |
| GB | 2 153 223 A | 8/1985 |
| JP | 61-198061 A2 | 9/1986 |
| JP | 63-108264 A | 5/1988 |
| JP | 03-060645 A2 | 3/1991 |
| JP | 4-053536 A2 | 2/1992 |
| JP | 5-63506 A | 8/1993 |
| JP | 06-508286 T2 | 9/1994 |
| JP | 7-255706 A | 10/1995 |
| JP | H08-080291 A | 3/1996 |
| JP | 2000-116629 A | 4/2000 |
| JP | 2002-085384 | 3/2002 |
| JP | 2002-272710 A | 9/2002 |
| JP | 2002-532165 A1 | 10/2002 |
| JP | 2003-159238 A | 6/2003 |
| JP | 2004-8413 A | 1/2004 |
| JP | 2004-500948 | 1/2004 |
| JP | 2004-191336 A | 7/2004 |
| JP | 2004-532079 A | 10/2004 |
| JP | 2005-011364 A | 1/2005 |
| JP | 2005-517463 A | 6/2005 |
| JP | 2005-522243 | 7/2005 |
| JP | 2005-211189 A | 8/2005 |
| JP | 2005-525141 A | 8/2005 |
| JP | 2005-245705 A | 9/2005 |
| JP | 2006-014789 | 1/2006 |
| JP | 2006-15148 A | 1/2006 |
| JP | 2006-109894 A | 4/2006 |
| JP | 2006-521555 A | 9/2006 |
| JP | 2006-280912 A | 10/2006 |
| JP | 2007-209549 A | 8/2007 |
| JP | 2007-209747 A | 8/2007 |
| JP | 2007-236686 | 9/2007 |
| JP | 2007-526460 A | 9/2007 |
| JP | 2008-022988 A | 2/2008 |
| JP | 2008-54884 A | 3/2008 |
| JP | 2008-079853 A | 4/2008 |
| JP | 2008-99988 A | 5/2008 |
| JP | 2008-099992 A | 5/2008 |
| JP | 2008-518662 A | 6/2008 |
| JP | 2008-534192 A | 8/2008 |
| JP | 2009-504273 A | 2/2009 |
| JP | 2009-509679 A | 3/2009 |
| JP | 2009-066385 A | 4/2009 |
| JP | 2009-078173 A | 4/2009 |
| JP | 2009-519064 A | 5/2009 |
| JP | 2009-254899 A2 | 8/2009 |
| JP | 2010-520036 A | 6/2010 |
| JP | 2011-511660 A | 4/2011 |
| JP | 2011-522593 A | 8/2011 |
| JP | 2014-516645 A | 7/2014 |
| KR | 2003-0061753 A | 7/2003 |
| WO | WO 92/02175 A1 | 2/1992 |
| WO | WO 92/04867 A1 | 4/1992 |
| WO | WO 93/00043 A1 | 1/1993 |
| WO | WO 95/10223 A2 | 4/1995 |
| WO | WO 95/15783 A1 | 6/1995 |
| WO | WO 97/08987 A1 | 3/1997 |
| WO | WO 97/10745 A1 | 3/1997 |
| WO | WO 97/034587 A2 | 9/1997 |
| WO | WO 97/48442 A1 | 12/1997 |
| WO | WO 98/24366 A2 | 6/1998 |
| WO | WO 99/27852 A1 | 6/1999 |
| WO | WO 99/59657 A1 | 11/1999 |

(56) References Cited

FOREIGN PATENT DOCUMENTS

| | | |
|---|---|---|
| WO | WO 00/35357 A1 | 6/2000 |
| WO | WO 00/35530 A1 | 6/2000 |
| WO | WO 00/74763 A2 | 12/2000 |
| WO | WO 01/43643 A1 | 6/2001 |
| WO | WO 01/93946 A1 | 12/2001 |
| WO | WO 02/00101 A2 | 1/2002 |
| WO | WO 02/05890 A2 | 1/2002 |
| WO | WO 02/30301 A1 | 4/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 02/100460 A2 | 12/2002 |
| WO | WO 02/101359 A2 | 12/2002 |
| WO | WO 03/020134 A2 | 3/2003 |
| WO | WO 03/026611 A2 | 4/2003 |
| WO | WO 03/030984 A2 | 4/2003 |
| WO | WO 03/039632 A2 | 5/2003 |
| WO | WO 2003/037403 A1 | 5/2003 |
| WO | WO 03/070099 A1 | 8/2003 |
| WO | WO 03/082091 A2 | 10/2003 |
| WO | WO 03/088851 A1 | 10/2003 |
| WO | WO 2003/083469 A2 | 10/2003 |
| WO | WO 03/099123 A1 | 12/2003 |
| WO | WO 04/006982 A3 | 1/2004 |
| WO | WO 04/022133 A2 | 3/2004 |
| WO | WO 04/085995 A2 | 10/2004 |
| WO | WO 2005/000118 A1 | 1/2005 |
| WO | WO 2005/023111 A1 | 3/2005 |
| WO | WO 2005/025413 A2 | 3/2005 |
| WO | WO 2005/084534 A1 | 9/2005 |
| WO | WO 2005/095965 A1 | 10/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/050032 A2 | 5/2006 |
| WO | WO 2006/105968 A1 | 10/2006 |
| WO | WO 2006/111741 A1 | 10/2006 |
| WO | WO 2006/121510 A2 | 11/2006 |
| WO | WO 2006/128034 A1 | 11/2006 |
| WO | WO 2006/132504 A1 | 12/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/073870 A2 | 7/2007 |
| WO | WO 2007/079530 A1 | 7/2007 |
| WO | WO 2007/091671 A1 | 8/2007 |
| WO | WO 2007/092585 A2 | 8/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2007/124411 A1 | 11/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/062032 A1 | 5/2008 |
| WO | WO 2008/081444 A2 | 7/2008 |
| WO | WO 2008/109845 A2 | 9/2008 |
| WO | WO 2008/153930 A1 | 12/2008 |
| WO | WO 2009/004627 A3 | 1/2009 |
| WO | WO 2009/008267 A1 | 1/2009 |
| WO | WO 2009/011138 A1 | 1/2009 |
| WO | WO 2009/027950 A2 | 3/2009 |
| WO | WO 2009/055693 A2 | 4/2009 |
| WO | WO 2009/071775 A1 | 6/2009 |
| WO | WO 2009/101112 A1 | 8/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/145920 A1 | 12/2009 |
| WO | WO 2009/148624 A1 | 12/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/101626 A1 | 9/2010 |
| WO | WO 2010/110916 A2 | 9/2010 |
| WO | WO 2010/120294 A1 | 10/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/058337 A2 | 5/2012 |
| WO | WO 2012/064802 A1 | 5/2012 |
| WO | WO 2012/149134 A1 | 11/2012 |
| WO | WO 2014/160893 A2 | 10/2014 |
| WO | WO 2017/191221 A1 | 11/2017 |

OTHER PUBLICATIONS

International Search Report and Written Opinion dated Oct. 4, 2012 in connection with PCT/US2012/035173.
International Preliminary Report on Patentability for PCT/US2012/035173 dated Nov. 7, 2013.
European Office Action dated Jun. 30, 2015 for Application No. 12723286.6.
European Intention to Grant dated Jan. 29, 2016 for Application No. 12723286.6.
European Intention to Grant dated Jun. 29, 2016 for Application No. 12723286.6.
European Intention to Grant dated Nov. 18, 2016 for Application No. 12723286.6.
European Notice of Opposition dated Mar. 13, 2018 in connection with European Application No. 12723286.6.
Extended European Search Report dated Sep. 22, 2017 in connection with European Application No. 17163359.7.
Chinese Office Action dated Mar. 24, 2015 for Application No. 201280021299.8.
Chinese Office Action dated Nov. 25, 2015 for Application No. 201280021299.8.
Chinese Office Action dated May 30, 2016 for Application No. 201280021299.8.
Japanese Office Action dated Mar. 22, 2016 for Application No. 2014-508547.
Japanese Notice of Reasons for Rejection dated Nov. 18, 2016 for Application No. 2014-508547.
Japanese Office Action dated Aug. 9, 2017 for Application No. 2014-508547.
[No Author Listed] Greiner Bio-One Preanalytics Catalogue, www.gbo.com/preanalytics. Feb. 2012. 76 pages.
[No Author Listed] Safe-T-Fill®: 100% Plastic Capillary Blood Collection Systems. RAM Scientific. [Month of publication not listed on copy] 2003. Last accessed Jun. 28, 2012 at http//www.ramsci.com.
[No Author Listed] Sof-Tact Manual. Date Unknown. 57 pages. (After reasonable inquiry, the undersigned believes this manual was available beginning 2001, but cannot determine the exact date of this publication.The year of publication is sufficiently earlier than the effective U.S. filing date and priority date so that the particular month and year of publication is not in issue. See MPEP 609.04(a).).
[No Author Listed], Whatman Neonatal Screening Cards-Capabilities. GE Healthcare. Dec. 2009; 12 pages. www.gelifesciences.com/whatman.
Angell et al., Silicon Micromechanical Devices. Scientific American. Apr. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J. Ind. Derm. 2007;127:1701-12. Epub Mar. 22, 2007.

(56) References Cited

OTHER PUBLICATIONS

Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Edelbroek et al., Dried blood spot methods in therapeutic drug monitoring: methods, assays, and pitfalls. Jun. 2009;31(3):327-36.
Elias, The Microscopic Structure of the Epidermis and Its Derivatives. In: Percutaneous Absorption—Mechanisms—Methodology. Bronaugh et al., eds. Marcell Dekker. 1989;3-12. (The year of publication is sufficiently earlier than the effective U.S. filing date and any foreign priority date so that the particular month of publication is not in issue. See MPEP 609.04(a)).
Fineberg et al., Use of an automated device for alternative site blood glucose monitoring. Diabetes Care. Jul. 2001;24(7):1217-20.
Fuhrer et al., Building a Smart Hospital using RFID technologies: Use Cases and Implementation. 2006; 14 pages.
Gomes et al., Evaluation of nanoparticles loaded with benzopsoralen in rat peritoneal exudate cells. Int J Pharm. Mar. 6, 2007;332(1-2):153-60. Epub Sep. 27, 2006.
Keevil. The analysis of dried blood spot samples using liquid chromatography tandem mass spectrometry. Clinic Biochem. Jul. 1, 2010; 44(2011):110-18.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104. (The year of publication is sufficiently earlier than the effective U.S. filing date and any foreign priority date so that the particular month of publication is not in issue. See MPEP 609.04(a)).
Majors. New directions in whole blood analysis: dried blood spot analysis and beyond. LCGC Chromatography Online. Jan. 1, 2011.
Matriano et al., Macroflux microprojection array patch technology: a new and efficient approach for intracutaneous immunization. Pharm Res. Jan. 2002;19(1):63-70.
McDade et al., What a drop can do: dried blood spots as a minimally invasive method for integrating biomarkers into population-based research. Demography. Nov. 2007;44(4):899-925.
McShane, Microcapsules as 'smart tattoo' glucose sensors: engineering systems with enzymes and glucose-binding sensing elements, *Top Fluor. Spec*., 2006, vol. 11, *Glc. Sens*., p. 131-163. (The year of publication is sufficiently earlier than the effective U.S. filing date and any foreign priority date so that the particular month of publication is not in issue. See MPEP 609.04(a)).
Mitragotri et al., Sonophoresis: Enhanced Transdermal Drug Delivery by Application of Ultrasound. In: Encl. of Pharm. Tech., vol. 14, Swarbrick, J., Boylan, J., (Eds.), vol. 14, 103-122, 1996. (After reasonable inquiry, the undersigned believes this was available in 1996, but cannot determine the exact date of this publication. The year of publication is sufficiently earlier than the effective U.S. filing date and priority date so that the particular month and year of publication is not in issue. See MPEP 609.04(a).).
Rousche et al., A method for pneumatically inserting an array of penetrating electrodes into cortical tissue. Annals of Biomedical Engineering. Jul. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95. (The year of publication is sufficiently earlier than the effective U.S. filing date and any foreign priority date so that the particular month of publication is not in issue. See MPEP 609.04(a)).
Rouse, Effects of mechanical flexion on the penetration of fullerene amino acid-derivatized peptide nanoparticles through skin. Nano Lett. Jan. 2007;7(1): 155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich, Polymeric systems for controlled drug release. Chem. Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. Aug. 2001;3:335-73.
Xia et al., Soft Lithography. Ann Rev Mater Sci. Aug. 1998;28:153-84.
U.S. Appl. No. 15/916,330, filed Mar. 9, 2018, Bernstein et al.
U.S. Appl. No. 15/285,034, filed Oct. 4, 2016, Davis et al.
U.S. Appl. No. 16/048,722, filed Jul. 30, 3018, Chickering et al.
U.S. Appl. No. 15/290,217, filed Oct. 11, 2016, Levinsin et al.
U.S. Appl. No. 14/805,678, filed Jul. 22, 2015, Haghgooie et al.
PCT/US2012/035173, Aug. 17, 2012, Invitation to Pay Additional Fees.
PCT/US2012/035173, Oct. 4, 2012, International Search Report and Written Opinion.
PCT/US2012/035173, Nov. 7, 2013, International Preliminary Report on Patentability.
EP 12723286.6, Jun. 30, 2015, European Office Action.
EP 12723286.6, Jan. 29, 2016, European Intention to Grant.
EP 12723286.6, Jun. 29, 2016, European Intention to Grant.
EP 12723286.6, Nov. 18, 2016, European Intention to Grant.
EP 12723286.6, Mar. 13, 2018, Notice of Opposition.
EP 17163359.7, Sep. 22, 2017, Extended European Search Report.
Summons to Attend Oral Proceedings dated Nov. 28, 2018 for Application No. EP 12723286.6.
U.S. Appl. No. 15/693,666, filed Sep. 1, 2017, Chickering et al.
U.S. Appl. No. 15/349,090, filed Nov. 11, 2016, Bernstein et al.
EP 12723286.6, Nov. 28, 2018, Summons to Attend Oral Proceedings.
[No Author Listed] Air-Tite Products Co., Inc.—Luer Slip. Oct. 14, 2008. Retrieved from the Internet: https://web.archive.org/web/20081014224752/https://www.air-tite-shop.com/c-6-luer-slip.aspx on Aug. 28, 2019. 2 pages.
[No Author Listed] Air-Tite Products Co., Inc.—Luer Lock. Oct. 14, 2008. Retrieved from the Internet: https://web.archive.org/web/20081023203858/https://www.air-tite-shop.com/c-7-luer-lock.aspx on Aug. 28, 2019. 2 pages.
Matsuura et al., Development of a blood extraction device for a miniature SMBG system. Dec. 27, 2007. Proceedings vol. 6799, BioMEMS and Nanotechnology III; 67990N (2007) https://doi.org/10.1117/12.758869. Event: SPIE Microelectronics, MEMS, and Nanotechnology, 2007, Canberra, ACT, Australia.
U.S. Appl. No. 15/916,330, filed Mar. 9, 2018, Davis et al.
U.S. Appl. No. 15/828,908, filed Dec. 1, 2017, Chickering et al.
U.S. Appl. No. 15/387,459, filed Dec. 21, 2016, Levinson et al.
U.S. Appl. No. 15/285,034, filed Oct. 4, 2016, Levinson et al.
U.S. Appl. No. 15/899,613, filed Feb. 20, 2018, Schott.
U.S. Appl. No. 16/048,722, filed Jul. 30, 2018, Chickering et al.
U.S. Appl. No. 15/290,217, filed Oct. 11, 2016, Levinson et al.
U.S. Appl. No. 15/297,253, filed Oct. 19, 2016, Brancazio.
U.S. Appl. No. 16/806,426, filed Mar. 2, 2020, Chickering et al.
U.S. Appl. No. 15/634,354, filed Jun. 27, 2017, Gonzalez-Zugasti et al.
U.S. Appl. No. 14/987,973, filed Jan. 5, 2016, Haghgooie et al.
U.S. Appl. No. 16/218,441, filed Dec. 12, 2018, Haghgooie et al.
U.S. Appl. No. 16/705,286, filed Dec. 6, 2019, Bernstein et al.
U.S. Appl. No. 16/321,123, filed Jan. 28, 2019, Barone et al.
European Office Action dated May 26, 2020, in connection with Application No. EP 17163359.7.
Interlocutory decision in Opposition proceedings (Art. 101(3)(a) and 106(2) EPC) for Application No. EP 16 162 360.8; Patent No. EP-B-3 087 919, mailed Apr. 22, 2021. 145 pages.

(56) References Cited

OTHER PUBLICATIONS

[No Author Listed], Definition of Stable. Merriam-Webster.com. Accessed Oct. 12, 2019 from <https://www.merriam-webster.com/dictionary/stable>. 2 pages.

[No Author Listed], Definition of Stable. Dictionary.com. Accessed Oct. 12, 2019 from <https://www.dictionary.com/browse/stable>. 3 pages.

[No Author Listed], Definition of Couple. Merriam-Webster.com. Accessed Oct. 12, 2019 from <https://www.merriam-webster.com/dictionary/coupled>. 2 pages.

[No Author Listed], Definition of Couple. Cambridge English Dictionary. Accessed Oct. 12, 2019 from <https://dictionary.cambridge.org/us/dictionary/english/coupled>. 1 page.

Strogatz, Chapter 2: Flows on the Line. In Nonlinear Dynamics and Chaos. Westview Press. Boulder, CO. 1994:15-43. 38 pages total.

* cited by examiner

SYSTEMS AND METHODS FOR COLLECTION AND/OR MANIPULATION OF BLOOD SPOTS OR OTHER BODILY FLUIDS

RELATED APPLICATIONS

This application is a continuation of U.S. patent application Ser. No. 13/456,546, filed Apr. 26, 2012, entitled "Systems and Methods for Collection and/or Manipulation of Blood Spots or Other Bodily Fluids," by Bernstein, et al., which claims the benefit of U.S. Provisional Patent Application Ser. No. 61/480,941, filed Apr. 29, 2011, entitled "Plasma or Serum Production and Removal of Fluids under Reduced Pressure," by Haghgooie, et al.; and of U.S. Provisional Patent Application Ser. No. 61/549,437, filed Oct. 20, 2011, entitled "Systems and Methods for Collection and/or Manipulation of Blood Spots or Other Bodily Fluids," by Bernstein, et al. Each of these is incorporated herein by reference.

FIELD OF INVENTION

The present invention generally relates to systems and methods for receiving blood (or other bodily fluids) from a subject, e.g., from or beneath the skin of a subject. In some cases, the blood (or other bodily fluids) may be deposited on a membrane or other substrate.

BACKGROUND

Phlebotomy or venipuncture is the process of obtaining intravenous access for the purpose of intravenous therapy or obtaining a sample of venous blood. This process is typically practiced by medical practitioners, including paramedics, phlebotomists, doctors, nurses, and the like. Substantial equipment is needed to obtain blood from a subject, including the use of evacuated (vacuum) tubes, e.g., such as the Vacutainer™ (Becton, Dickinson and company) and Vacuette™ (Greiner Bio-One GmBH) systems. Other equipment includes hypodermic needles, syringes, and the like. However, such procedures are complicated and require sophisticated training of practitioners, and often cannot be done in non-medical settings. Accordingly, improvements in methods of obtaining blood or other fluids from the skin are still needed.

SUMMARY

The present invention generally relates to systems and methods for receiving blood (or other bodily fluids) from a subject, e.g., from or beneath the skin of a subject. In some cases, the blood (or other bodily fluids) may be deposited on a membrane or other substrate. The subject matter of the present invention involves, in some cases, interrelated products, alternative solutions to a particular problem, and/or a plurality of different uses of one or more systems and/or articles.

In one aspect, the present invention is generally directed to a device for receiving blood from the skin and/or from beneath the skin of a subject. In one set of embodiments, the device includes a substance transfer component for receiving blood from the skin of the subject, a vacuum chamber having an internal pressure less than atmospheric pressure before blood is received into the device from the substance transfer component, and a substrate for absorbing blood received from the subject In another set of embodiments, the device includes a substance transfer component for receiving the bodily fluid from the skin of the subject, a vacuum chamber having an internal pressure less than atmospheric pressure before the bodily fluid is received into the device from the substance transfer component, and a substrate for absorbing the bodily fluid received from the subject The invention, in another set of embodiments, is generally directed to a method. In one set of embodiments, the method includes acts of applying a device to the skin of a subject, where in some cases, the device may apply reduced pressure to the skin of the subject, and withdrawing blood from the skin of the subject into the device such that at least a portion of the blood contacts a substrate for absorbing the blood.

The method in another set of embodiments, includes an act of receiving blood into a device by applying reduced pressure to the skin of the subject, where at least a portion of the blood within the device contacts a substrate for absorbing the blood.

In one aspect, the present invention is generally directed to a simple, one-piece, low-profile, high acceleration, high energy, actuation mechanism for inserting microneedles (or other objects) into the skin for the purpose of receiving substances, such as blood or interstitial fluid. In one set of embodiments, a device of the invention is actuated by a deployment actuator which can provide advantages in ease of operation, speed of operation, reduction or elimination of pain, etc.

In another aspect, the present invention is directed to a method of making one or more of the embodiments described herein, for example, devices for receiving a fluid such as blood from a subject. In another aspect, the present invention is directed to a method of using one or more of the embodiments described herein, for example, devices for receiving a fluid such as blood from a subject.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
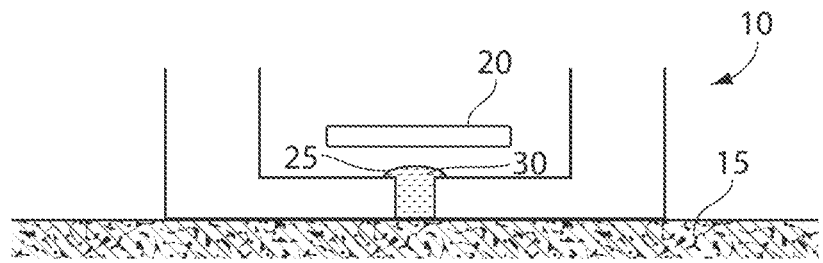
FIGS. 1A-1B illustrate devices including a substrate for absorbing blood or other bodily fluids, according to certain embodiments of the invention.

The present invention generally relates to systems and methods for receiving blood (or other bodily fluids) from a subject, e.g., from or beneath the skin of a subject. In some cases, the blood (or other bodily fluids) may be deposited on a membrane or other substrate. For example, blood may be absorbed in a substrate, and dried in some cases to produce a dried blood spot. In one aspect, the present invention is generally directed to devices and methods for receiving blood from a subject, e.g., from the skin, using devices including a substance transfer component (which may contain, for example, one or more microneedles), and directing the blood on a substrate, e.g., for absorbing blood. The substrate, in some embodiments, may comprise filter paper or cotton-based paper. After absorption of some blood onto the substrate, the substrate may be removed from the device and shipped or analyzed. In some cases, the device itself may be shipped or analyzed. For example, in some embodiments, a portion of the device may be sealed such that the substrate is contained within an airtight portion of the device, optionally containing desiccant. Other aspects are generally directed at other devices for receiving blood (or other bodily fluids), kits involving such devices, methods of making such devices, methods of using such devices, and the like.

As mentioned, certain aspects of the present invention are directed to substrates for absorbing blood and/or other bodily fluids, for example, a blood spot membrane. Thus, in some embodiments, blood spots may be produced on a blood spot membrane. In these cases, a channel within the device may have a small volume relative to the volume of a blood spot membrane which may be very porous and may collect fluid. The blood spot membrane is used to collect fluid in certain embodiments. The blood spot membrane is not used to separate cells/plasma (as opposed to the separation membranes discussed herein), in certain cases. Fluid may fill all, or a portion of, the blood spot membrane. A second hydrophobic membrane may be positioned on top of the collection membrane in some embodiments. Once fluid contacts the hydrophobic membrane, fluid collection may cease. The blood spot membrane may remain in the device to dry and can then be removed from the device. In some embodiments, the blood spot membrane may be removed from the device and dried outside of the device. In some cases, the membrane is not dried. If a vacuum is used to draw blood towards the blood spot membrane, the vacuum may be released prior to removal of the blood spot membrane from the device, at least in some embodiments.

In one set of embodiments, the substrate is contained within a device for receiving blood from the skin of a subject. Examples of such devices, and details of such devices able to contain a substrate for absorbing blood and/or other bodily fluids, are discussed in detail below. Additional examples of devices in which a substrate for absorbing blood and/or other bodily fluids may be utilized can be found in U.S. Provisional Patent Application Ser. No. 61/480,977, filed Apr. 29, 2011, entitled "Delivering and/or Receiving Fluids," by Gonzales-Zugasti, et al., incorporated herein by reference in its entirety for all purposes.

In one set of embodiments, the substrate for absorbing blood may comprise paper, e.g., that is able to absorb blood or other bodily fluids received by the device. The substrate may be able to partially or wholly absorb any blood (or other bodily fluid) that it comes into contact with. For example, the substrate may comprise filter paper, cellulose filters, cotton-based paper, e.g., made from cellulose filters, cotton fibers (e.g., cotton linters), glass fibers, or the like. Specific non-limiting examples that are commercially available include Schleicher & Schuell 903™ or Whatman 903™ paper (Whatman 903™ Specimen Collection Paper) (Whatman International Limited, Kent, UK), or Ahlstrom 226 specimen collection paper (Ahlstrom Filtration LLC, Mount Holly Springs, Pa.). In some embodiments, the paper may be one that is validated in compliance with the requirements of the CLSI (Clinical and Laboratory Standards Institute) LA4-A5 consensus standard. However, other materials may also be used for the substrate for absorbing blood, instead of and/or in addition to paper. For example, the substrate for absorbing blood (or other bodily fluids) may comprise gauze, cloth, cardboard, foam, foamboard, paperboard, a polymer, a gel, or the like. In some cases, the absorbent substrate may have a surface area of at least about 0.001 $m^2/g$, at least about 0.003 $m^2/g$, at least about 0.005 $m^2/g$, at least about 0.01 $m^2/g$, at least about 0.03 $m^2/g$, at least about 0.05 $m^2/g$, at least about 0.1 $m^2/g$, at least about 0.3 $m^2/g$, at least about 0.5 $m^2/g$, or at least about 1 $m^2/g$. In some cases, the absorbent substrate may have a surface area of about 100 $g/m^2$ to about 200 $g/m^2$, or about 150 $g/m^2$ to about 200 $g/m^2$.

The blood (or other bodily fluid) may be absorbed into the substrate such that the blood becomes embedded within fibers or other materials forming the substrate, and/or such that the blood becomes embedded in spaces between the fibers or other materials forming the substrate. For example, the blood may be held within or on the substrate mechanically and/or chemically (e.g., via clotting and/or reaction with fibers or other materials forming the substrate).

In some cases, the substrate may absorb a relatively small amount of blood. For example, less than about 1 ml, less than about 800 microliters, less than about 600 microliters, less than about 500 microliters, less than about 400 microliters, less than about 300 microliters, less than about 200 microliters, less than about 100 microliters, less than about 80 microliters, less than about 60 microliters, less than about 40 microliters, less than about 30 microliters, less than about 20 microliters, less than about 10 microliters, or less than about 1 microliter of blood may be absorbed into the substrate.

The substrate may be of any shape or size. In some embodiments, the substrate may be substantially circular, although in other embodiments, other shapes are possible, e.g., square or rectangular. The substrate may have any suitable area. For example, the substrate may be large enough to contain only one spot, of blood (e.g., of the above volumes), or more than one spot in some embodiments. For example, the substrate may have an area of no more than about 1 $cm^2$, no more than about 3 $cm^2$, no more than about 5 $cm^2$, no more than about 7 $cm^2$, no more than about 10 $cm^2$, no more than about 30 $cm^2$, no more than about 50 $cm^2$, no more than about 100 $cm^2$, no more than about 300 $cm^2$, no more than about 500 cm², no more than about 1000 cm², or no more than about 3000 cm².

Figure 4:
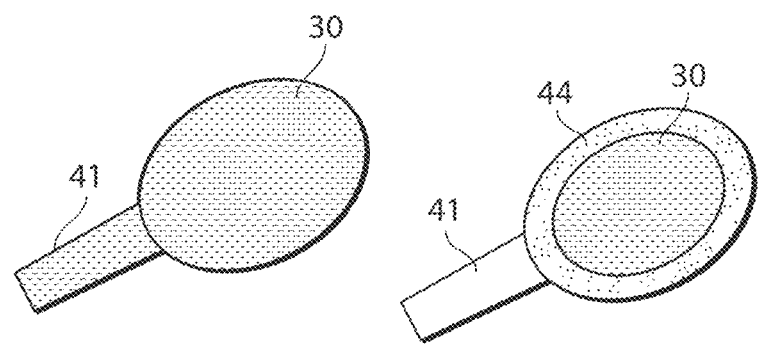
FIG. 4 illustrates various substrates including tabs or handles, in certain embodiments of the invention.

In some embodiments, a "tab" or a handle, or other separate portion, may be present on or proximate the substrate, e.g., to facilitate analysis and/or manipulation of the absorbed blood or other bodily fluid. The handle may be any portion that can be used to manipulate the substrate. For example, a handle may be used to remove the substrate from the device for subsequent shipping and/or analysis, e.g., without requiring a person to touch the blood spot itself in order to manipulate the substrate. The handle may be formed from the substrate, and/or different material, for example, plastic, cardboard, wood, metal, etc. In some cases, the handle may surround all, or at least a portion of, the substrate. Non-limiting examples of such handles are illustrated in FIG. 4. For instance, in FIG. 4A, a tab 41 is formed as an integral part of the substrate 20. In FIG. 4B, a separate handle 44 surrounds substrate 20, including a separate tab 41.

In certain embodiments, the substrate may include stabilizers or other agents, e.g., for stabilizing and/or treating the blood in the substrate. Non-limiting examples of stabilizers include chelating agents, enzyme inhibitors, or lysing agents. Examples of chelating agents include, but are not limited to, EDTA (ethylenediaminetetraacetic acid) or dimercaprol. Examples of enzyme inhibitors include, but are not limited to, protease inhibitors (e.g., aprotinin, bestatin, calpain inhibitor I and II, chymostatin, E-64, leupeptin or N-acetyl-L-leucyl-L-leucyl-L-argininal, alpha-2-macroglobuline, Pefabloc SC, pepstatin, PMSF or phenylmethanesulfonyl fluoride, TLCK, a trypsin inhibitor, etc.) or reverse transcriptase inhibitors (e.g., zidovudine, didanosine, zalcitabine, stavudine, lamivudine, abacavir, emtricitabine, entecavir, apricitabine, etc.). Non-limiting examples of lysing agents include distilled water or guanidinium thiocyanate.

One non-limiting example of a substrate able to absorb blood and/or other bodily fluids within a device may be seen in FIG. 1A. In this figure, device 10 is placed on the surface of skin 15. Additional examples of such devices are discussed in more detail below, and/or in documents incorporated herein by reference. In FIG. 1A, blood 30 (or another bodily fluid, such as interstitial fluid) from skin 15 enters device 10 via a substance transfer component 25. For example, a flow activator of the substance transfer component 25, such as one or more microneedles (not shown here) may be used to cause blood to flow into device 10 towards substrate 20. In this figure, substrate 20 is positioned so that blood entering device 10 will come into contact with substrate 20. At least a portion of the blood entering the device may be absorbed into the substrate. It should be understood, however, that other configurations are also possible. Thus, the substrate may be positioned at any suitable location within a device, e.g., such that blood (or other bodily fluid) is able to come into contact with at least a portion of the substrate when blood is received into the device. As non-limiting examples, a substrate may be positioned flush with the skin or in a recess, e.g., of the of the substance transfer component, the substrate may be positioned further away from the substance transfer component such that the blood flows through a portion of the device (e.g., through one or more channels) in order to reach the substrate, or the like. In some embodiments, the substrate may be positioned no more than about 1 mm, no more than about 2 mm, no more than about 3 mm, no more than about 4 mm, or no more than about 5 mm away from the surface of the skin when the device is applied to the surface of the skin of a subject.

Another embodiment is now described with reference to FIG. 1B; further details of this and other devices in accordance with certain aspects of the present invention are also described in further detail below. In this example figure, device 10 is applied to the skin 15 of a subject. The device in this figure is self-contained, i.e., such that the device is able to function to withdraw blood from a subject to produce plasma or serum without requiring external connections such as an external source of vacuum, an external source of power, or the like. In other embodiments, however, the device need not be self-contained.

A vacuum or a reduced pressure less than atmospheric or ambient pressure may be used to facilitate the movement of blood 30 into the device, as follows. The vacuum may be contained within device 10, for example, within vacuum chamber 35. Blood 30 on the skin 15 of the subject may become exposed to the vacuum or reduced pressure, which causes the blood to enter device 10, e.g., through applicator region 40 into inlet 42 of channel 45, moving towards substrate 50, which can be a substrate for absorbing blood, e.g., as previously discussed. Thus, when blood 30 reaches substrate 50, at least a portion of the blood may become absorbed into substrate 50. In some cases, some blood may also pass through substrate 50 into vacuum chamber 35.

Figure 1B:
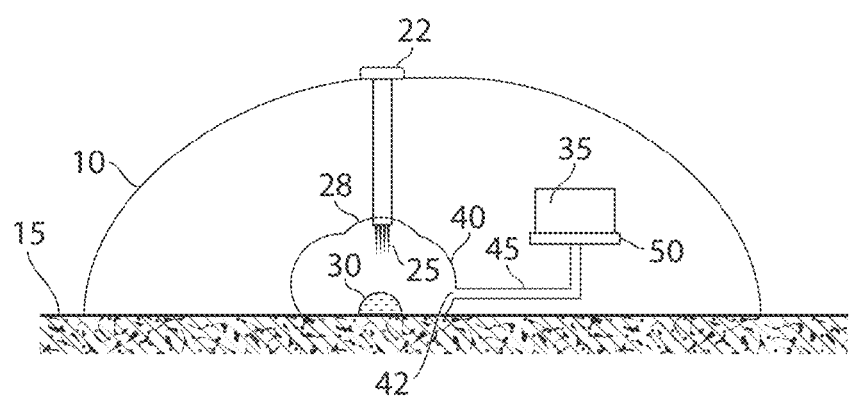

Upon actuation of the device shown in FIG. 1B, for example, remotely or by pressing button 22, flow activators 25 are deployed into skin 15 of the subject. The flow activators may include one or more needles or microneedles, or other flow activators as discussed in detail below and/or in documents incorporated herein by reference. As shown in this figure, the deployment of flow activators 25 into skin 15 of the subject may be accomplished using a deployment actuator 28, or by other techniques such as those described herein. The deployment actuator 28 may include suitable components to deploy the flow activators 25, such as a button, a switch, a lever, a slider, a dial, a compression spring, a Belleville spring, a servo, rotary or linear electric motor, and/or a pneumatic apparatus, or other suitable device.

Figure 2A:
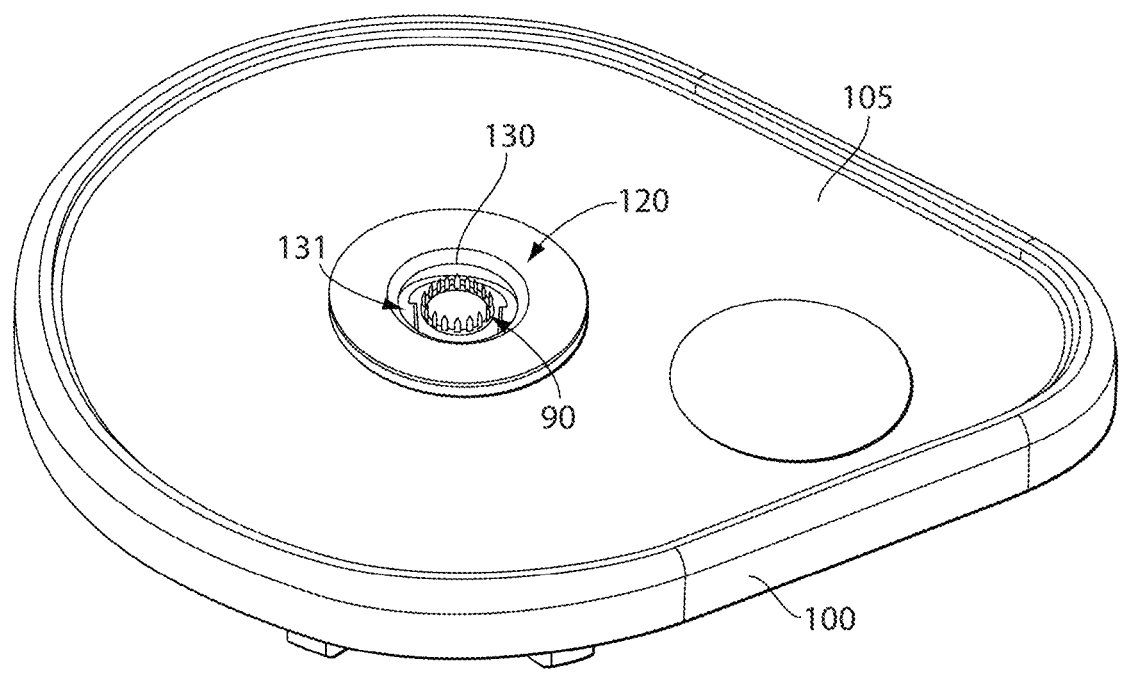
FIGS. 2A-2B illustrate additional devices including a substrate for absorbing blood or other bodily fluids, according to various embodiments of the invention
Figure 2B:
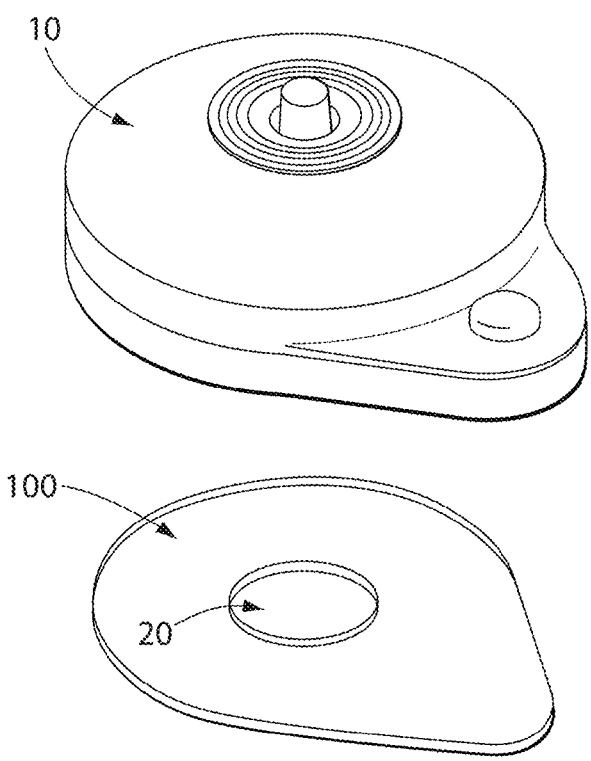

As another non-limiting example, FIG. 2A shows an underside of a fluid receiving device 10 according to another embodiment of the invention; a top view of the device may be seen in FIG. 2B. FIG. 2A shows a fluid transporter 120 that includes an opening 130, an applicator region 131, and a flow activator 90. In this embodiment, the flow activator 90 includes one or more needles. As described in more detail below, the needles may be extended from the opening 130 to pierce a subject's skin, and then retracted back into the opening to allow blood or other fluid to enter the opening 130. That is, to use device 10 to receive blood from a subject, the base 100 may be placed on the skin so that the opening 130 is adjacent the skin. Thereafter, a device actuator may be depressed to cause the needles to be deployed, piercing the skin and causing blood to be released. Blood may enter the opening and be collected in the storage chamber 140. In one embodiment, blood may flow into the storage chamber 140 as a result of a relatively low pressure (vacuum) in the device 10 that draws blood from the opening 130 and into a storage chamber internally of the device (not shown here). A substrate 20 for absorbing blood and/or other bodily fluids may be positioned within the storage chamber, and/or as part of base 100 of the device as is shown in FIG. 2B.

After being absorbed on the substrate, the blood (or other bodily fluid) may be allowed to dry and/or clot, in certain embodiments of the invention. Clotting of blood may occur naturally, e.g., upon exposure to air. Drying or clotting, in some cases, may occur through gaseous exchange with the external environment, and/or with an internal environment contained within the device, e.g., an environment with a relatively low relative humidity. For example, the internal or external environment may be one in which the relative humidity is less than about 50%, less than about 30%, less than about 25%, less than about 20%, less than about 15%, less than about 10%, or less than about 5%. As a specific example, the internal environment may be "pre-packaged" such that the device has a relatively low relative humidity before use, and/or a dessicant may be used to control the relative humidity within the device. In some cases, the device may include a heat source, such as a resistive heater, to facilitate drying and/or clotting.

Thus, in some embodiments, the device may contain desiccant. The desiccant may be "pre-packaged" in the device, and/or desiccant may be added after blood or other bodily fluids has been received into the device. For example, a cover or a lid may be put on the device after blood has been received into the device, where the cover or lid contains desiccant. Non-limiting examples of desiccant potentially suitable for the device include solid desiccants such as $P_2O_5$, $CaSO_4$, $CaCl_2$, silica, or the like. The desiccant may be present in the same chamber within the device as the substrate comprising absorbed blood (or other bodily fluids), and/or the desiccant may be present in a different chamber within the device, e.g., one in gaseous communication with the substrate.

In one set of embodiments, after blood is received on the substrate, the device may be manipulated in order to create an airtight seal around the substrate. For example, an internal portion of the device may be sealed off to create an airtight seal, e.g., forming an enclosed airtight chamber surrounding the substrate. In some embodiments, for instance, a portion of the device may be moveable or sealable to create an airtight portion within the device, or a cover or a lid may be added to the device, and/or brought into position on the device to create an airtight portion. A user of the device may manipulate the device to create the airtight portion, and/or the device may itself create the airtight portion, for example, upon removal of at least a portion of the substance transfer component from the subject. For example, in one set of embodiments, a cover or lid may be used to seal the substance transfer component from the external environment surrounding the device, thereby preventing exchange of gases from the substrate with the external environment. The cover or lid may be formed out of any suitable material, e.g., plastic, rubber, metal, or the like. As another example, a valve may be closed or the device may close a valve in order to form an airtight portion within the device containing the substrate. For example, a valve may be positioned on channel 45 in FIG. 1B that can be closed (manually or automatically) in order to form an airtight seal around substrate 50.

In some embodiments, blood or other bodily fluids may be stored within the device for later use and/or analysis, e.g., on a substrate such as previously discussed. For example, the substrate and/or the device may, in some embodiments, be sent to a clinical and/or laboratory setting, e.g., for analysis or storage. In some embodiments, the entire device and/or substrate may be sent to a clinical and/or laboratory setting; in other embodiments, however, only a portion of the device and/or substrate may be sent to a clinical and/or laboratory setting. For example, the substrate may be removed from the device, or a module containing the substrate may be removed from the device, e.g., for shipping or other transport. In some cases, the substrate and/or the device may be shipped using any suitable technique (e.g., by mail, by hand, etc.). Blood or other bodily fluids may be present during shipping in dried form (e.g., clotted), or while at least partially liquid, in some cases. In certain instances, the subject may give the substrate and/or the device to appropriate personnel at a clinical visit. For instance, a doctor may prescribe a device as discussed above for use by the subject, and at the next doctor visit, the subject may give the doctor the substrate and/or the device.

According to certain embodiments, the substrate and/or the device may be shipped with only minimal preparation, for example, where blood or other bodily fluids are present as spots (e.g., dry spots) on the substrates. In some cases, as discussed herein, the spots may be relatively small. For instance, the volume of the blood in a spot, prior to drying, may be less than about 100 microliters, less than about 80 microliters, less than about 60 microliters, less than about 40 microliters, less than about 30 microliters, less than about 20 microliters, less than about 10 microliters, or less than about 1 microliter. In certain embodiments, shipping may occur at room or ambient temperature, without the need for ice or dry ice to maintain constant or colder temperatures. In some cases, shipping may also be performed without the need for biohazard labeling.

In some embodiments, the substrate and/or the device may be contained within a suitable shipping container, for instance, an envelope or a box. For example, the envelope may be a paper envelope, a cardboard envelope, or the like. The box may be, for example, a paper box, a cardboard box, a plastic box, a metal box, etc. In some cases, the shipping container may be padded, e.g., with cloth, plastic bubbles, Styrofoam pellets, etc. In some cases, the shipping container may be airtight and/or the shipping container may contain a desiccant. In some embodiments, the device and/or the substrate may be placed in a shipping container in such a form that the substrate is exposed to at least the air within the shipping container, and the use of an airtight container and/or desiccant may serve to preserve blood or other bodily fluids absorbed within the substrate in a relatively dry state. Examples of desiccant include those described herein. In other embodiments, however, desiccant and/or an airtight container may not be necessary. For example, as previously discussed, the device itself may contain desiccant, or the blood may be dried on the substrate such that further precautions are unnecessary and the substrate may be shipped or otherwise manipulated (e.g., analyzed) while exposed to ambient conditions, and/or without any subsequent preservation steps.

In one aspect, the device and/or the substrate may include, and/or may be shipped with, a tracking apparatus. The tracking apparatus may be present as part of the device or as a part of a cover or lid for the device, and/or the tracking apparatus may be separate from the device but designed to be shipped with the device and/or the substrate. For example, the tracking apparatus may be formed as or be contained within a shipping container such as an envelope or a box for shipping the device and/or the substrate. In some cases, for example, the tracking apparatus may be attached to the envelope or box, or the tracking apparatus may be part of a holder designed to be shipped with the device and/or the substrate.

In one set of embodiments, the tracking apparatus may include an RFID transmitter or "tag." A suitable scanner may be able to determine the RFID tag, e.g., when a shipping container such as an envelope or a box for shipping the device and/or the substrate is received, e.g., at a clinical and/or laboratory setting. As another example, a scannable target may be used as a tracking apparatus. For example, the scannable target may be a bar code, such as a 1- or 2-dimensional barcode, and may code information based on lines, colors, patterns, shapes, or any other features or combinations of features. In some embodiments, a scanner able to scan the scannable target may also be used. For example, in one set of embodiments, prior to or during use, the device may be held next to the scannable target such that the device is able to scan the scannable target, e.g., in order to activate the device, or to record data from the device, etc. As additional non-limiting examples, in other embodiments, the scannable target may be formed as part of the substrate, and the scannable target may be tracked after the substrate has received blood, before or after the substrate has been shipped, before or after analysis of blood (or other bodily fluid) on the substrate, etc.

In some cases, more than one substrate for absorbing blood and/or other fluids may be present in the device. For instance, more than one substrate for absorbing blood and/or other bodily fluids may be stacked together. For instance, in certain cases, excess blood (or other bodily fluid) is received by the device, and blood is able to saturate some of the substrates within the device. By use of multiple substrates in a stacked configuration, some substrates (e.g., a middle substrate) may be used for subsequent analysis, while other substrates (e.g., on the top and/or bottom) are simply present to absorb excess blood.

However, as mentioned, in some embodiments, more than one substrate may be used for subsequent analysis. In some cases, the substrates may also be arranged separately from each other, e.g., as is illustrated with respect to FIG. 3. In this figure, substrates 31, 32, 33, and 34 are arranged about a central region 39. Blood received into the device may pass through central region 35 to some or all of substrates 31, 32, 33, and 34, and some or all of these may then be subsequently analyzed, e.g., for different analytes such as those discussed herein.

Other types of substrates or blood spot membranes may also be present within the device. For example, in some embodiments, the device may include a separation membrane that is impermeable to blood cells and other substances. The separation membrane may be positioned anywhere in the device, e.g., before or after blood contacts a substrate for absorbing blood within the device. Fluid received from the subject may flow through a separation membrane, and the received fluid may include components of various sizes. For example, the device may receive blood that includes blood cells, clotting factors, proteins, and blood plasma, among other components. Larger components such as blood cells and other larger substances may not be able to pass through the separation membrane while blood plasma is free to pass. If anticoagulant is not introduced to the blood plasma, the blood plasma, which contains clotting factors such as fibrinogen, may clot, thereby resulting in a solid clot component and a liquid component. This liquid component is known as serum, which is blood plasma without fibrinogen or other clotting factors. This serum can be collected via aspiration or other suitable method out of the storage chamber, leaving the blood clots in the storage chamber. If anticoagulant is introduced to the blood plasma, the blood plasma will not clot and blood plasma can be collected out of the storage chamber instead. Thus, the embodiments described throughout the specification may be used to produce plasma or serum. More details regarding plasma and serum production can be found in U.S. Provisional Pat. Apl. Ser. No. 61/480,941, entitled "Plasma or Serum Production and Removal of Fluids Under Reduced Pressure," filed on Apr. 29, 2011 by Haghgooie, et al., incorporated herein by reference in its entirety.

Figure 3:
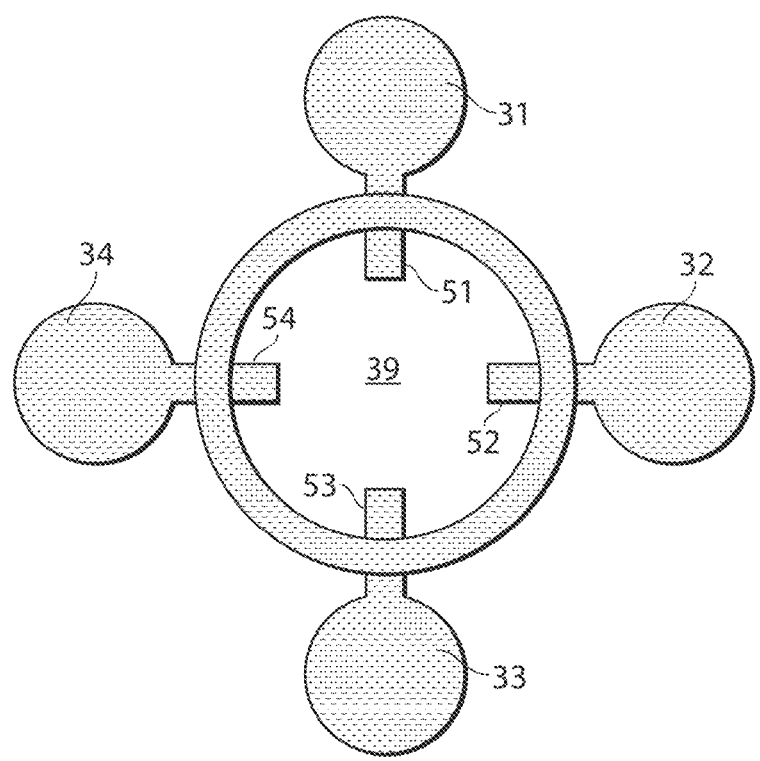
FIG. 3 illustrates one embodiment including a plurality of substrates.

Also shown in FIG. 3 are optional beading disruptors 51, 52, 53, and 54. Beading disruptors generally disrupt the "pooling" of bodily fluids such as blood on the surface of the skin and allow blood to flow to a desired location, e.g., to a substrate. Thus, as is shown in FIG. 3, beading disruptors 51, 52, 53, and 54 are used to direct blood towards substrates 31, 32, 33, and 34. It should be understood that this is by way of example only; in other embodiments, there may be 1, 2, 3, or any other suitable number of beading disruptors. In yet other embodiments, there may be no beading disruptors present. Non-limiting examples of additional beading disruptors suitable for use in certain embodiments of the invention are disclosed in U.S. Provisional Patent Application Ser. No. 61/480,960, filed Apr. 29, 2011, entitled "Systems and Methods for Collecting Fluid from a Subject," by Haghgooie, et al., incorporated herein by reference in its entirety.

Figure 5A:
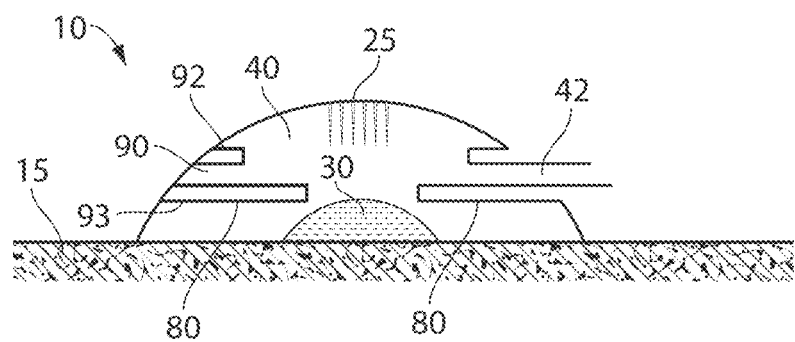
FIGS. 5A-5B illustrate an applicator region in accordance with certain embodiments of the invention.
Figure 5B:
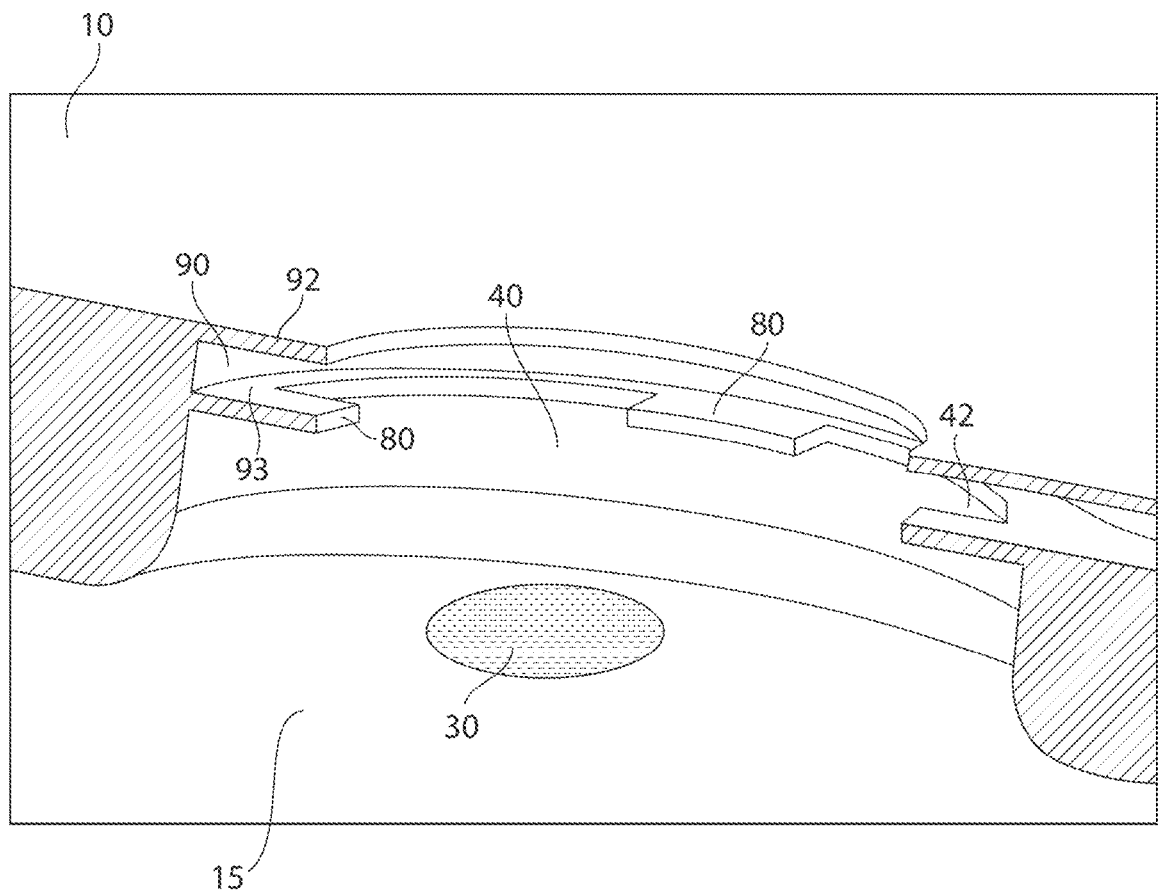

One non-limiting example of such a device comprising a beading disruptor is now described with reference to FIGS. 5A and 5B. In these figures, device 10 is used to receive blood or other bodily fluids from the skin and/or from beneath the skin of a subject. Device 10 is shown positioned on skin 15 of a subject. Bodily fluid 30 is caused to reach the surface of the skin using one or more flow activators that include, for example, microneedles 25 as shown in this figure. In other embodiments, however, as discussed below and/or in documents incorporated herein by reference, other flow activator arrangements may be used in addition to and/or instead of flow activators that include microneedles 25. The bodily fluid collects on the surface of skin 15 within applicator region 40, and at least some of the bodily fluid may enter device 10 through inlet 42. FIG. 5A shows a side view while FIG. 5B shows an angled view of a cross-section of an applicator region of certain devices.

The bodily fluid 30 on the surface of the skin typically will from a "pool" or a "bead" of liquid on the surface of the skin. However, this beading of the liquid may prevent, or at least delay, the movement of the bodily fluid 30 to inlet 42. To counter the natural tendency of the bodily fluid to form a bead on the surface, one or more beading disruptors may be used. As depicted in FIGS. 5A and 5B, beading disruptor 80 can take the form of one or more protrusions extending from a portion of the surface defining applicator region 40. However, in other embodiments, the beading disruptor may take other forms, instead of and/or in addition to one or more protrusions. Upon contact of bodily fluid 30 with beading disruptor 80, at least a portion of the bead of fluid may be deformed or otherwise be caused to move towards inlet 42 for entry into the device, e.g., for processing, analysis, storage, etc. as is discussed in detail below.

In some embodiments, the applicator region may include a capillary that may facilitate fluid flow. Fluid may move along the capillary with, or without, capillary action, e.g. it may be moved due to a vacuum, pneumatic force, gravity feed, or other suitable manner. Additionally, the capillary may be of any cross-sectional shape, length, diameter, and is not limited to any particular arrangement. The some cases, the capillary may be a capillary slit, e.g., including a relatively narrow groove. However, a capillary slit is only one arrangement and others are possible. For example, fluid may flow through a closed tube of any suitable cross-sectional shape. Also, it should be noted that beading disruptor 80 and capillary slit 90 are not necessarily required in all embodiments; in certain cases, one or both of these may be absent. As shown in FIG. 5B, capillary slit 90 may be positioned such that it is in fluidic communication with inlet 42. In this embodiment, a single capillary slit is shown that forms a closed circuit or circle along the surface of the applicator region 40 (note that FIG. 5B has been cut in half for clarity). However, in other embodiments, more than one capillary may be present and/or the capillary may not necessarily form a closed circuit along the surface of the applicator region 40. In addition, in this figure, capillary slit 90 is depicted as being oriented substantially parallel to the opening of the applicator region and skin 15 of the subject, although in other embodiments, other orientations are also possible. Capillary slit 90, in this example, is illustrated as having two substantially parallel walls 92, 93, and a cross-sectional shape that is substantially rectangular.

A bodily fluid 30 on the surface of the skin may come into contact with capillary slit 90 during use, and at least a portion of the bodily fluid may then flow along capillary slit 90, e.g., due to capillary action. The capillaries may thereby guide bodily fluid 30 towards inlet 42 into the device. As shown in FIG. 5, beading disruptor 80 is formed as part of the bottom plane of capillary slit 90, such that at least a portion of the bead of bodily fluid may be caused to enter capillary slit 90, and the fluid can then be moved towards inlet 42, e.g., as previously discussed.

Figure 6A:
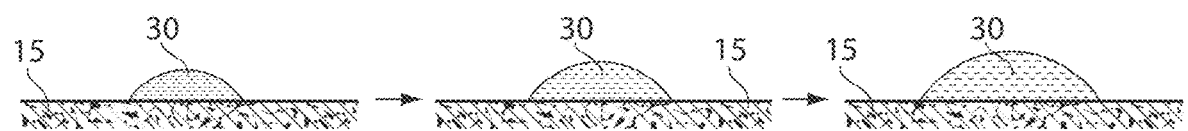
FIGS. 6A-6B illustrate the formation of a pool of bodily fluid on the surface of the skin, in certain embodiments of the invention.

The applicator region may contain, in one set of embodiments, one or more beading disruptors for disrupting the pooling of bodily fluids on the surface of the skin. This is now illustrated with reference to the example shown in FIG. 6. In FIG. 6A, a bodily fluid 30, such as blood, is present on the surface of the skin 15, e.g., transported thereto by one or more flow activators such as is discussed herein. The bodily fluid typically forms a bead or pool on the surface of the skin, instead of wetting the skin. The shape of the bead (e.g., the contact angle) may be controlled by the condition of the skin (for example, its hydrophobicity) and/or the bodily fluid on the skin. For example, the bodily fluid may pool on the skin of the subject at a contact angle of about 30°, about 40°, about 45°, about 50°, about 55°, etc. in a substantially circular region on the surface of the skin. In many cases, the skin is relatively hydrophobic, thereby causing the bodily fluid to form a bead instead of wetting or spreading on the surface of the skin. Furthermore, as more bodily fluid enters the bead, the bead typically grows in size while keeping substantially the same shape. Thus, before the bead is able to contact a surface of the applicator region, a certain amount of bodily fluid must flow from the body into the bead on the surface of the skin.

Figure 6B:
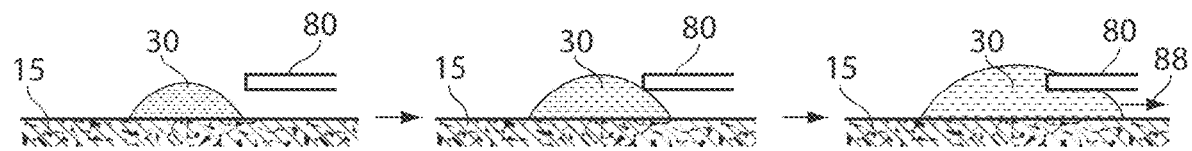

In FIG. 6B, beading disruptor 80 is also shown, in addition to bodily fluid 30 on the surface of skin 15. Beading disruptor 80 is shaped and positioned to disrupt the shape of bodily fluid 30 to prevent or at least alter the ability of bodily fluid 30 to pool on the surface of the skin. Thus, in this example, bodily fluid exiting the skin within the applicator region (e.g., from the center of the applicator region) will first come into contact with the beading disruptor, which can disrupt the shape of the pool of bodily fluid on the surface of the skin. In some cases, as is shown in this figure, at least a portion of bodily fluid 30 may be caused to move away from the pool of fluid, e.g., towards an inlet of the device, or another suitable location as is shown by arrow 88, due to the presence of beading disruptor 80.

The beading disruptor may take any of a variety of forms. In one set of embodiments, the beading disruptor is present within an applicator region, such as a recess, in which a bodily fluid is transported thereto by a flow activator, for example, one or more needles and/or microneedles. More than one beading disruptor may also be present, in some embodiments.

In one set of embodiments, in a protrusion having a first end in contact with the applicator region and a second end that is located closest to the geometrical center of the applicator region, a ratio of the width of the first end to the distance between the first end and the second end, may be about 1, greater than 1, or less than 1. This ratio may have any suitable value. For example, the ratio may be about 1 (i.e., such that the protrusion is substantially square), less than 1, or greater than 1. As specific non-limiting examples, this ratio may be less than or greater than 1, less than or greater than 2, less than or greater than 3, less than or greater than 4, less than or greater than 5, less than or greater than 7, less than or greater than 10, etc.

It should be understood, however, that the beading disruptor is not necessarily limited to projections or protrusions. For example, in certain embodiments, the beading disruptor may be connected at two portions to the applicator region, e.g., forming a "span" across the applicator region. In some embodiments the beading disruptor includes the geometric center of the applicator region, but in other embodiments, the geometric center of the applicator region is not included. More complex shapes may also be used in some embodiments, for example, where the beading disruptor physically contacts the applicator region at three ends, at four ends (e.g., defining an "X" or a cross shape), or more in some cases.

In one set of embodiments, the beading disruptor may comprise a "shelf" or a "lip" along a portion of the applicator region. In some, the beading disruptor may be positioned along a portion of the applicator region, for example, such that an imaginary plane can be positioned that divides the applicator region into two halves that have the same volume such that only one of the two halves comprises the beading disruptor.

In some embodiments, the beading disruptor can be positioned to facilitate the flow of a bodily fluid to an inlet to the device, e.g., to the inlet of a channel such as a microfluidic channel within the device. In some cases, as is discussed below, the beading disruptor may form a portion of a capillary that facilitates the flow of a bodily fluid to an inlet to the device.

In one set of embodiments, the applicator region contains one or more capillaries that can facilitate the flow of a bodily fluid to an inlet of the device, or to a substrate for absorbing blood or other fluids. A non-limiting example of a capillary is shown with respect to FIG. 7A. In this figure, the surface of a portion of applicator region 40 of device 10 is illustrated, including a capillary 90 that is in fluid communication with inlet 42 of the device. In this figure, capillary 90 is defined by walls 92, 93 which are substantially parallel to each other, thereby forming capillary 90. In some embodiments, at least a portion of capillary 90, such as one or both of walls 92, 93, may also be used as a beading disruptor.

Figure 7A:
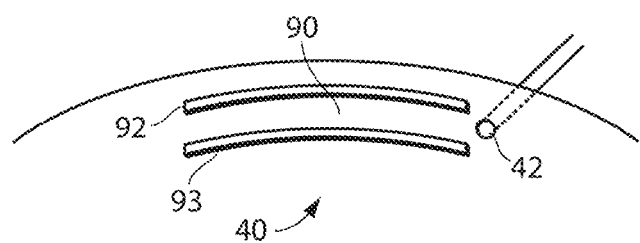
FIGS. 7A-7B illustrate various capillaries in accordance with certain embodiments of the invention.
Figure 7B:
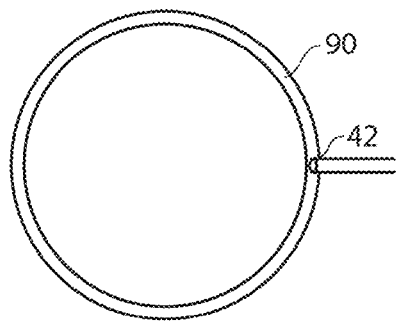

Although only one capillary is shown in FIG. 7A, in other embodiments, more than one capillary may be present, which may be lead to one or more inlets of the device. The capillary can have any suitable configuration to facilitate the flow of a bodily fluid along at least a portion of the capillary, e.g., through capillary action. In some cases, the capillary may encircle or circumscribe at least a portion of the applicator region. For instance, the capillary may form a closed circuit such that the flow of bodily fluid in any direction along the capillary will reach the inlet. One example of this can be seen in FIG. 7B with capillary 90 and inlet 42.

The capillary may have any suitable size. For example, the capillary may have an average cross-sectional dimension (e.g., perpendicular to the flow of fluid therein) of less than about 10 mm, less than about 9 mm, less than about 8 mm, less than about 7 mm, less than about 6 mm, less than about 5 mm, less than about 4 mm, less than about 3 mm, or less than about 2 mm, less than about 1 mm, less than about 500 microns, less than about 300 microns, or less than about 100 microns. For example, the capillary may have an average cross-sectional diameter of between about 100 and about 700 micrometers, or between about 300 and about 500 micrometers. The average cross-sectional dimension may be constant or may change along the capillary, e.g., to promote flow towards the inlet. The capillary can have any cross-sectional shape, for example, circular, oval, triangular, irregular, square or rectangular (having any aspect ratio), or the like. The capillary may have, in certain embodiments, a cross-sectional shape and/or area that remains substantially constant throughout the capillary.

In some embodiments, the entire capillary may be exposed to the applicator region; in other embodiments, however, a portion of the capillary may not necessarily be open to or exposed to the applicator region. In some cases, some or all of the capillary is in fluidic communication with the applicator region, for example such that substantially each portion of the capillary can be reached by a fluid within the applicator region. For instance, in certain embodiments, no portion of the capillary is further than about 10 micrometers, about 5 micrometers, about 3 micrometers, or about 1 micrometer away from a portion of the applicator region, as determined by flow of a fluid from the applicator region to the capillary. In some embodiments, no portion of the capillary may be further than about 5 mm, about 3 mm, about 1 mm, about 500 micrometers, about 300 micrometers, about 100 micrometers, about 50 micrometers, about 30 micrometers, or about 10 micrometers away from a portion of the applicator region, as determined by flow of a fluid from the applicator region to the capillary, e.g., depending on the size of the applicator region. In some embodiments, no portion of the applicator region is greater than about 5 mm, about 3 mm, about 1 mm, about 500 micrometers, about 300 micrometers, about 100 micrometers, about 50 micrometers, about 30 micrometers, or about 10 micrometers away from a portion of the capillary The capillary may be positioned in any suitable location within the applicator region. In some cases, a capillary may be positioned near an inlet in the applicator region, or near a substrate for absorbing blood such that at least some blood is directed towards the substrate.

The invention, in one set of embodiments, involves the determination of a condition of a subject. Blood or other bodily fluids associated with the skin, for example, absorbed on a substrate, may be analyzed, e.g., for the presence of one or more analytes, for instance, as an indication of a past, present and/or future condition of the subject, or to determine conditions that are external to the subject. Determination may occur, for instance, visually, tactilely, by odor, via instrumentation, etc. In one aspect, accordingly, the present invention is generally directed to various devices for receiving blood, or other bodily fluids, from the skin and/or from beneath the skin of a subject. In the description that follows, the discussion of blood is by way of example only, and in other embodiments, other fluids may be received from the skin in addition to and/or instead of blood, for example, interstitial fluid.

In some cases, blood or other bodily fluids (e.g., interstitial fluid) received from the subject, e.g., on a substrate, may be used for indication of a past, present and/or future condition of the subject. Thus, the condition of the subject to be determined may be one that is currently existing in the subject, and/or one that is not currently existing, but the subject is susceptible or otherwise is at an increased risk to that condition. The condition may be a medical condition, e.g., diabetes or cancer, or other physiological conditions, such as dehydration, pregnancy, illicit drug use, or the like. In one set of embodiments, the materials may include a diagnostic agent, for example, one which can determine an analyte within the subject, e.g., one that is a marker for a disease state.

In one set of embodiments, blood (or other bodily fluid) on a substrate may accordingly be determined, e.g., to determine a past, present and/or future condition of the subject. Any suitable method may be used to determine or analyze the blood present on the substrate. For example, one or more portions of the substrate may be used (e.g., cut out or punched), or the entire substrate may be used, e.g., without requiring any punching out of portions of the substrate. In some cases, for instance, the blood may be present as one or more dried spots, and portions of the substrate may be cut off (e.g., punched out as holes, cut with scissors, etc.) for analysis. As mentioned, in some embodiments, more than one substrate may be present within the device, and in some cases, some or all of the substrates can be used.

In some embodiments, the blood (or other bodily fluid) on the substrate may be analyzed on the substrate, e.g., using techniques such as spectroscopy, microscopy, etc. In other embodiments, the substrate (or cut portions thereof) may be eluted to remove at least a portion of the blood (or other bodily fluids) on the substrate. As one example, blood can be eluted out from the substrate using saline, such as phosphate buffered saline, optionally containing detergents such as Tween. The resultant eluent can be subsequently analyzed to determine analytes within the blood. Any suitable technique can be used for analysis, many of which are commercially available or are known to those of ordinary skill in the art, for example, spectroscopy, HPLC analysis, ELISA, etc.

Non-limiting examples of such analytes include, but are not limited to: acarboxyprothrombin; acylcarnitine; adenine phosphoribosyl transferase; adenosine deaminase; albumin; a-fetoprotein; amino acids such as arginine (Krebs cycle), histidine/urocanic acid, homocysteine, phenylalanine/tyrosine, or tryptophan, etc.; andrenostenedione; antipyrine; arabinitol enantiomers; arginase; benzoylecgonine (cocaine); biotinidase; biopterin; C-reactive protein; carnitine; carnosinase; CD4; ceruloplasmin; chenodeoxycholic acid; chloroquine; cholesterol; cholinesterase; conjugated 1-b hydroxycholic acid; cortisol; creatine kinase; creatine kinase MM isoenzyme; cyclosporin A; D-penicillamine; de-ethylchloroquine; dehydroepiandrosterone sulfate; DNA (PCR), e.g., to detect acetylator polymorphism, alcohol dehydrogenase, a 1-antitrypsin, cystic fibrosis, Duchenne/Becker (e.g., muscular dystrophy), glucose-6-phosphate (e.g., dehydrogenase), hemoglobinopathies (e.g., A, S, C, E, D-Punjab, beta-thalassemia, hepatitis B virus, HCMV, HIV-1, HTLV-1, Leber hereditary optic, neuropathy, MCAD, mRNA, PKU, *Plasmodium vivax*, sexual differentiation); 21-deoxycortisol; desbutylhalofantrine; dihydropteridine reductase; diptheria/tetanus antitoxin; erythrocyte arginase; erythrocyte protoporphyrin; esterase D; fatty acids/acylglycines; free b-human chorionic gonadotropin; free erythrocyte prophyrin; free thyroxine (FT4); free tri-iodothyroine (FT3); fumarylacetoacetase; galactose/gal-1-phosphate; galactose-1-phosphate uridyl transferase; gentamicin; glucose; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase i; 17-a hydroxyprogesterone; hypoxanthine phosphoribosyl transferase; Immunoreactive trypsin (CF); lactate; lead; lipoproteins (a), B/A-1, and b; lysozyme; mefloquine; netilmicin; phenobarbitone; phenytoin; phytanic/pristanic acid; progesterone; prolactin; prolidase; purine nucleoside; phosphorylase; quinine; reverse tri-iodothyronine (rT3); selenium; serum pancreatic lipase; sissomicin; somatomedin C; specific antibodies (e.g., adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae, Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, or yellow fever virus); spectic antigens (e.g., hepatitis B virus or HIV-1); succinylacetone; sulfadoxine; theophylline; thyrotropin (TSH); or throxine (T4).

As mentioned, in certain aspects, the substrate may be contained within a device for receiving blood from the skin of a subject. As used herein, the phrase "from the skin" is used to mean from the top or outer surface of the skin, from within the skin, and/or from beneath the skin. Likewise, "to the skin" is used to mean to the top or outer surface of the skin, to within the skin, and/or to beneath the skin. In some embodiments, for example, the present invention is generally directed to devices and methods for receiving or extracting blood or other bodily fluids from a subject, e.g., from the skin and/or from beneath the skin, using devices having a substance transfer component (which may include, for example, one or more microneedles and/or other skin insertion objects). The device may also contain, in some embodiments, a storage chamber and/or a vacuum chamber having an internal pressure less than atmospheric pressure prior to receiving blood or other bodily fluids. Additional non-limiting examples of devices can be found in U.S. Provisional Patent Application Ser. No. 61/480,977, filed Apr. 29, 2011, entitled "Delivering and/or Receiving Fluids," by Gonzales-Zugasti, et al., incorporated herein by reference in its entirety. In various embodiments, those devices may include one or more substrates as discussed herein, e.g., for absorbing blood or other bodily fluids.

In some cases, the device may pierce the skin of the subject, and fluid can then be delivered and/or received from the subject. The subject is usually human, although non-human subjects may be used in certain instances, for instance, other mammals such as a dog, a cat, a horse, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like.

The device may be used once, or multiple times, depending on the application. For instance, a device may be used once to receive blood, then the device and/or substrate, or a portion thereof, may be shipped, or a device may be used multiple times, e.g., by replacing a module or a substrate and replacing it with a fresh module or substrate.

In some embodiments, the device may be relatively small. For example, the device may be handheld or be applied to the skin of a subject, e.g., using an adhesive, as is discussed below. The device may be self-contained in some embodiments, i.e., such that the device is able to function to withdraw blood (or other bodily fluids) from a subject and cause at least some of the blood to be absorbed into the substrate, e.g., without requiring external connections such as an external source of vacuum, an external source of power, or the like. For instance, a vacuum source within the device, e.g., a vacuum chamber, may be used to draw blood to the substrate.

The received fluid may be any suitable bodily fluid, such as interstitial fluid, other skin-associated material, mucosal material or fluid, whole blood, perspiration, saliva, plasma, tears, lymph, urine, plasma, or any other bodily fluid, or combinations thereof. Substances received from a subject can include solid or semi-solid material such as skin, cells, or any other substance from the subject. Substances that can be delivered to a subject in accordance with some embodiments of the invention include diagnostic substances, therapeutic substances such as drugs, and the like. Various embodiments of the invention are described below in the context of delivering or receiving a fluid, such as blood, from or through the skin. It is to be understood that in all embodiments herein, regardless of the specific exemplary language used (e.g., receiving blood), the devices and methods of other embodiments of the invention can be used for receiving any substance from the skin and/or from beneath the skin of the subject, and/or for delivering any substance to the subject, e.g. to the skin and/or a location beneath the skin of the subject.

In some cases, the device can be applied to the skin, and activated to receive fluid from the subject. The device, or a portion thereof, may then be processed to determine the fluid and/or an analyte within the fluid, alone or with an external apparatus. For example, fluid may be received from the device, and/or the device may contain sensors or agents able to determine the fluid and/or an analyte suspected of being contained in the fluid.

In some embodiments, the substance transfer component may include one or more skin insertion objects, such as needles, microneedles, lancets, blades, knives, protrusions, or other suitable object. As used herein, a "skin insertion object," may be inserted into any organ, tissue or portion of a subject and is not restricted for use with only skin.

In one set of embodiments, the device includes a substance transfer component able to deliver to or receive fluid from the subject. As used herein, "substance transfer component" is any component or combination of components that facilitates movement of a substance or a fluid from one portion of the device to another, and/or from the device to the subject or vice versa. The substance transfer component may include an opening of any size and/or geometry that is constructed to receive fluid into the device. For example, an opening of a substance transfer component may lie in a two-dimensional plane or the opening may include a three-dimensional cavity, hole, groove, slit, etc. In some embodiments, the substance transfer component may also include one or more microneedles or other skin insertion objects, arranged to cause fluid to be released from the subject, e.g., by piercing the skin of a subject. In some embodiments, if fluid may partially or fully fill an enclosure surrounding a skin insertion object or other object, then the enclosure can define at least part of a substance transfer component. A substance transfer component may include any other suitable fluid transporter or flow activator. Other components including partially or fully enclosed channels, microfluidic channels, tubes, wicking members, vacuum containers, etc. can be, or be a part of, a substance transfer component.

If needles or microneedles are used, they may be solid or hollow, i.e., blood or other fluid may travel in and/or around the needles or microneedles into or from the device. In some cases, the needles or microneedles may also be removed from the subject, e.g., after insertion into the skin, for example, to increase the flow of blood or other fluids from the subject. In one set of embodiments, the substance transfer component includes solid needles that are removed from the skin and a cup or channel to direct the flow of blood or other bodily fluids.

It should be noted that a skin insertion object or other flow activator need not be included with all embodiments as the device may not necessarily employ a mechanism for causing fluid release from the subject. For instance, the device may receive fluid that has already been released due to another cause, such as a cut or an abrasion, fluid release due to a separate and independent device, such as a separate lancet, an open fluid access such as during a surgical operation, and so on. Additionally, fluid may be introduced into the device via urination, spitting, pouring fluid into the device, etc. If included, a skin insertion object or other substance transfer component may physically penetrate, pierce, and/or or abrade, chemically peel, corrode and/or irritate, release and/or produce electromagnetic, acoustic or other waves, other otherwise operate to cause fluid release from a subject. The substance transfer component may include a moveable mechanism, e.g., to move a needle, or may not require movement to function. For example, the substance transfer component may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of an element to cause fluid release from a subject.

In some aspects, the device may include a support structure, such as a housing. The housing may be used, as discussed herein, for applying the substance transfer component to the surface of the skin of the subject, e.g., so that fluid may be delivered and/or received from the skin of the subject. In some cases, the housing may immobilize the substance transfer component such that the substance transfer component cannot move relative to the housing; in other cases, however, the substance transfer component, or a portion thereof, may be able to move relative to the housing. In one embodiment, as a non-limiting example, the substance transfer component is immobilized relative to the housing, and the deployment actuator is positioned within the device such that application of the device to the skin causes at least a portion of the substance transfer component to pierce the skin of the subject. In some cases, as previously discussed, the housing encloses a deployment actuator.

In some embodiments, the deployment actuator, or a portion of the deployment actuator, may move from a first position to a second position. For example, the first position may be one where the deployment actuator has attached thereto a substance transfer component that is not in contact with the skin (e.g., a skin insertion object of the substance transfer component may be contained within a recess of the substance transfer component), while the second position of the deployment actuator may be one where the substance transfer component does contact the skin, e.g., to pierce the skin. The deployment actuator may be moved using any suitable technique, e.g., manually, mechanically, electromagnetically, using a servo mechanism, or the like. In one set of embodiments, for example, the deployment actuator may be moved from a first position to a second position by pushing a button on the device, which causes the deployment actuator to move (either directly, or through a mechanism linking the button with the deployment actuator). Other mechanisms (e.g., dials, levers, sliders, etc., as discussed herein) may be used in conjunction of or instead of a button. In another set of embodiments, the deployment actuator may be moved from a first position to a second position automatically, for example, upon activation by a computer, upon remote activation, after a period of time has elapsed, or the like. For example, in one embodiment, a servo connected to the deployment actuator is activated electronically, moving the deployment actuator from the first position to the second position. In some cases, the deployment actuator may include a triggering mechanism that initiates deployment.

In some cases, the deployment actuator and/or the substance transfer component may also be moved from the second position to the first position (or some other position). For example, after fluid has been delivered and/or received from the skin, e.g., using a substance transfer component, the deployment actuator may be moved, which may move the substance transfer component away from contact with the skin. The deployment actuator may be moved from the second position to the first position using any suitable technique, including those described above, and the technique for moving the deployment actuator from the second position to the first position may be the same or different as that moving the deployment actuator from the first position to the second position.

In some cases, the device may be able to draw skin towards the substance transfer component. For example, in one set of embodiments, the device may include a vacuum interface or region. The interface or region may be connected with a vacuum source (external and/or internal to the device), and when a vacuum is applied, skin may be drawn towards the device, e.g., for contact with a substance transfer component, such as one or more needles or microneedles.

In one set of embodiments, the device includes a deployment actuator able to drive a substance transfer component into the skin, e.g., so that the device can receive a fluid from the skin of a subject, and/or so that the substance transfer component can deliver a substance to a subject, e.g. deliver a substance to the skin and/or to a location beneath the skin of a subject. The deployment actuator may be a structure that can be deformed using unaided force (e.g., by a human pushing the structure), or other forces (e.g., electrically-applied forces, mechanical interactions or the like), but is able to restore its original shape after the force is removed or at least partially reduced. For example, the structure may restore its original shape spontaneously, or some action (e.g., heating) may be needed to restore the structure to its original shape. In one set of embodiments, the deployment actuator may include a flexible concave member or a reversibly deformable structure that is moveable between a first configuration and a second configuration. The deployment actuator may be formed out a suitable elastic material, in some cases. For instance, the structure may be formed from a plastic, a polymer, a metal, etc. In one set of embodiments, the structure may have a concave or convex shape. For instance, the edges of the structure may be put under compressive stress such that the structure "bows" out to form a concave or convex shape. A person pushing against the concave or convex shape may deform the structure, but after the person stops pushing on the structure, the structure may be able to return to its original concave or convex shape, e.g., spontaneously or with the aid of other forces as previously discussed. In some cases, the device may be bistable, i.e., having two different positions in which the device is stable.

In certain embodiments, quick and/or high velocity, and/or high force and/or pressure application of skin insertion objects to the skin, such as microneedles, or other substance transfer components, may in certain embodiments result in lower pain or painless deployment. Without wishing to be bound by any theory, it is believed that higher velocities, forces, etc., may result in faster penetration of the objects into the skin, which results in less damage to the skin, and thus less pain. In addition, relatively rapid insertions may give a subject less sensation of pain, and/or less time to become apprehensive to the insertion, thereby resulting in lower perceived pain. Examples of devices able to deliver objects quickly and/or at high velocity, and/or with high force and/or pressure are disclosed in detail herein, and include, but are not limited to, snap domes and other deployment actuators such as those described below.

Figure 8A:
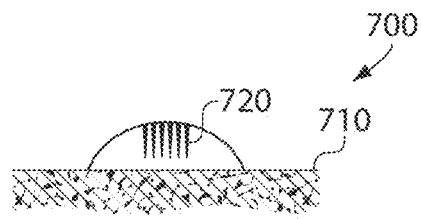
FIGS. 8A-8C illustrate a device in still another embodiment, illustrating a deployment actuator.
Figure 8B:
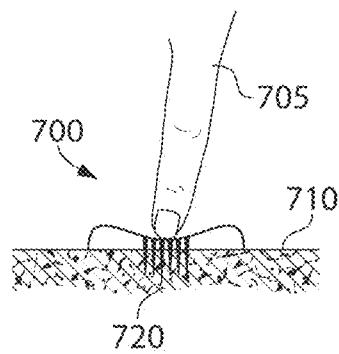
Figure 8C:
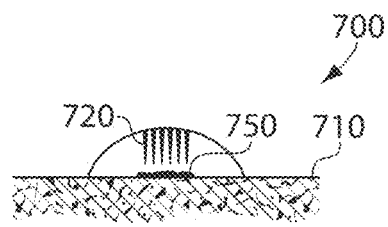

An example of a deployment actuator is now illustrated with respect to FIG. 8. In FIG. 8A, structure 700 has a generally concave shape, and is positioned on the surface of skin 710. Structure 700 also includes a substance transfer component 720 for insertion into the skin. In FIG. 8B, a person (indicated by finger 705) pushes onto structure 700, deforming at least a portion of the structure and thereby forcing a substance transfer component 720 into at least a portion of the skin. In FIG. 8C, after the person releases structure 700, the structure is allowed to return to its original position, e.g., spontaneously, lifting substance transfer component 720 out of the skin. In some cases, e.g., if the substance transfer component includes needles or other skin insertion objects that are sufficiently large or long, blood or other fluids 750 may come out of the skin through the holes created by the needles, and optionally the fluid may be collected by the device for later storage and/or use, as discussed herein.

Devices of the invention can provide significant advantage in some embodiments. For example, deployment actuators able to move substance transfer components in short time periods, and/or at high velocities, and/or with high forces, and/or with high pressure, and/or drive relatively short substance transfer components such as skin insertion objects or microneedles relatively deeply into the skin and/or through the skin, and/or any combination of the above can provide significant advantage. In some embodiments, these features can provide better control of substance delivery or receipt. Better mechanical stability can be provided in some cases by shorter substance transfer components (e.g., bending and/or buckling can be avoided) and relatively shorter substance transfer components, designed to be driven relatively completely (for example, through nearly all of their entire length) into the skin may offer better control of penetration in some embodiments. If better control of penetration can be achieved, better delivery or receiving can also be achieved in some cases, for example, resulting in less pain or essentially painless deployment.

Moreover, if substance transfer components are used to deliver a substance such as a pharmaceutical composition into or through the skin, more precise delivery can be provided, according to certain embodiments. With better, precise control over depth of insertion of the substance transfer components (e.g., by using devices designed to insert the substance transfer components essentially fully), and/or the substance transfer components contain and/or are coated with a pharmaceutical composition, then more control exists over the amount of pharmaceutical substance inserted into the skin by the substance transfer components, in some embodiments. Furthermore, quick and/or high velocity, and/or high force and/or pressure application of skin insertion objects to the skin may in certain embodiments result in lower pain or painless deployment.

According to one set of embodiments, many devices as discussed herein use various techniques for delivering and/or receiving fluid, for example, in connection with substance transfer components, skin insertion objects, or the like. For example, one or more needles and/or microneedles, a hygroscopic agent, a cutter or other piercing element, an electrically-assisted system, or the like may be used in conjunction with a snap dome or other device as described above. Additional examples of such techniques are described herein and/or in the applications incorporated herein. It is to be understood that, generally, fluids may be delivered and/or received in a variety of ways, and various systems and methods for delivering and/or receiving fluid from the skin are discussed below and/or in the applications incorporated herein. In some embodiments, for example, techniques for piercing or altering the surface of the skin to transport a fluid are discussed, for example, using a needle such as a hypodermic needle or microneedles, chemicals applied to the skin (e.g., penetration enhancers), jet injectors or other techniques such as those discussed below, etc.

As an example, in one embodiment, a needle such as a hypodermic needle can be used to deliver and/or receive fluid to or from the skin. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

If needles are present, the needles may be of any suitable size and length, and may be solid or hollow. The needles may have any suitable cross-section (e.g., perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than about 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least 5:1, at least about 7:1, at least about 10:1, at least about 15:1, at least about 20:1, at least about 25:1, at least about 30:1, etc.

In one embodiment, the needle is a microneedle. As an example, microneedles such as those disclosed in U.S. Pat. No. 6,334,856, issued Jan. 1, 2002, entitled "Microneedle Devices and Methods of Manufacture and Use Thereof," by Allen, et al., may be used to deliver and/or receive fluids or other materials to or from a subject. The microneedles may be hollow or solid, and may be formed from any suitable material, e.g., metals, ceramics, semiconductors, organics, polymers, and/or composites. Examples include, but are not limited to, pharmaceutical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluoroethylene, polymethyl methacrylate, polyacrylic acid, or polyesters.

In some cases, more than one microneedle may be used. For example, arrays of microneedles may be used, and the microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of microneedles. In some embodiments, the device may have at least 3 but no more than 5 needles or microneedles (or other skin insertion objects), at least 6 but no more than 10 needles or microneedles, or at least 11 but no more than 20 needles or microneedles. Typically, a microneedle will have an average cross-sectional dimension (e.g., diameter) of less than about a micron. It should be understood that references to "needle" or "microneedle" as discussed herein are by way of example and ease of presentation only, and that in other embodiments, more than one needle and/or microneedle may be present in any of the descriptions herein.

Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

In some cases, the microneedles may be present in an array selected such that the density of microneedles within the array is between about 0.5 needles/mm$^2$ and about 10 needles/mm$^2$, and in some cases, the density may be between about 0.6 needles/mm$^2$ and about 5 needles/mm$^2$, between about 0.8 needles/mm$^2$ and about 3 needles/mm$^2$, between about 1 needles/mm$^2$ and about 2.5 needles/mm$^2$, or the like. In some cases, the needles may be positioned within the array such that no two needles are closer than about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, about 0.03 mm, about 0.01 mm, etc.

In another set of embodiments, the needles (or microneedles) may be chosen such that the area of the needles (determined by determining the area of penetration or perforation on the surface of the skin of the subject by the needles) allows for adequate flow of fluid to or from the subject. The microneedles may be chosen to have smaller or larger areas (or smaller or large diameters), so long as the area of contact for the microneedles to the skin is sufficient to allow adequate blood flow from the subject to the device. The needles or microneedles may have any suitable cross-sectional area. For example, in certain embodiments, each microneedle may be selected to have a cross-sectional area of at least 5 nm$^2$, at least about 100 nm$^2$, at least about 500 nm$^2$, at least about at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, or at least about 25,000 microns$^2$. For example, in certain embodiments, the microneedles may be selected to have a combined skin-penetration area of at least about 500 nm$^2$, at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, at least about 35,000 microns$^2$, at least about 100,000 microns$^2$, etc., depending on the application.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the needles or microneedles may have a maximum penetration into the skin, or insertion depth, of no more than about 3 mm, no more than about 2 mm, no more than about 1.75 mm, no more than about 1.5 mm, no more than about 1.25 mm, no more than about 1 mm, no more than about 900 microns, no more than about 800 microns, no more than about 750 microns, no more than about 600 microns, no more than about 500 microns, no more than about 400 microns, no more than about 300 microns, no more than about 200 microns, no more than about 175 micrometers, no more than about 150 micrometers, no more than about 125 micrometers, no more than about 100 micrometers, no more than about 75 micrometers, no more than about 50 micrometers, etc. In certain embodiments, the needles or microneedles may be selected so as to have a maximum insertion depth of at least about 50 micrometers, at least about 100 micrometers, at least about 300 micrometers, at least about 500 micrometers, at least about 1 mm, at least about 2 mm, at least about 3 mm, etc.

In certain embodiments, relatively long needles or microneedles may be used. For instance, the average length of the needles or microneedles in the device may be at least about 200 micrometers, at least about 300 micrometers, at least about 400 micrometers, at least about 500 micrometers, at least about 600 micrometers, at least about 750 micrometers, at least about 800 micrometers, at least about 900 micrometers, at least about 1,000 micrometers, at least about 1,200 micrometers, at least about 1,500 micrometers, at least about 1,700 micrometers, or at least about 2,000 micrometers in some embodiments.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound or a vasodilator to assist with the flow of blood from the skin of the subject. The coating may comprise a drug or other therapeutic agent such as those described herein. The drug or other therapeutic agent may be one used for localized delivery (e.g., of or proximate the region to which the coated needles or microneedles are applied), and/or the drug or other therapeutic agent may be one intended for systemic delivery within the subject.

At least some the skin insertion objects may be at least partially coated by a substance such as a drug, analgesic or agent by using dip or spray coating or other suitable technique. Thus, the substance may be delivered to the skin by the substance dissolving or otherwise detaching from the substance transfer component at or in the skin or other subject site. Alternately, the substance may be delivered after a substance transfer component penetrates the subject, e.g., in a way similar to a hypodermic needle. For example, a skin insertion object of the substance transfer component may be inserted into the skin, and a substance may be pumped or pushed through a hole, groove or other channel of the skin insertion object (e.g., by a high pressure gas).

In one embodiment, the fluid is received manually, e.g., by manipulating a plunger on a syringe. In another embodiment, the fluid can be delivered and/or received from the skin mechanically or automatically, e.g., using a piston pump or the like. Fluid may also be received using vacuums such as those discussed herein. For example, vacuum may be applied to a conduit, such as a needle, in fluidic communication with a bodily fluid in order to draw up at least a portion of the fluid from the pooled region. In yet another embodiment, fluid is received using capillary action (e.g., using a microfluidic channel or hypodermic needle having a suitably narrow inner diameter). In still another embodiment, pressure may be applied to force fluid out of the needle.

In some embodiments, the device may comprise a cutter able to cut or pierce the surface of the skin. The cutter may comprise any mechanism able to create a path through which fluids may be delivered and/or received from the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the delivery and/or receiving of fluid from the skin. In one embodiment, a cutter is used to create such a pathway and removed, then fluid may be delivered and/or received via this pathway. In another embodiment, the cutter remains in place within the skin, and fluid may be delivered and/or received through a conduit within the cutter.

In some embodiments, fluid may be received using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a perm-selective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby receiving a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device may comprise a substance transfer component in the form of an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a substance transfer component in the form of a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, surfactants, etc.

The device may also contain, in some embodiments, a vacuum source. In some cases, the vacuum source is one that is self-contained within the device, i.e., the device need not be connected to an external vacuum source (e.g., a house vacuum) during use of the device to receive blood from the skin. For example, in one set of embodiments, the vacuum source may include a vacuum chamber having a pressure less than atmospheric pressure before blood (or other fluid) is received into the device, i.e., the vacuum chamber is at a "negative pressure" (that is, negative relative to atmospheric pressure) or a "vacuum pressure" (or just having a "vacuum"). For example, the vacuum in the vacuum chamber may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg, i.e., below atmospheric pressure. However, in other embodiments, it should be understood that other pressures may be used and/or that different methods may be used to produce other pressures (greater than or less than atmospheric pressure). As non-limiting examples, an external vacuum or a mechanical device may be used as the vacuum source; various additional examples are discussed in detail herein.

As a specific, non-limiting example, in one embodiment, a device may be used to receive fluid without an external power and/or a vacuum source. Examples of such devices include skin patches, strips, tapes, bandages, or the like. For instance, a skin patch may be contacted with the skin of a subject, and a vacuum created through a change in shape of a portion of the skin patch or other device (e.g., using a shape memory polymer), which may be used to deliver and/or receive fluid from the skin. As a specific example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum.

Thus, in some cases, the device is "pre-packaged" with a suitable vacuum source (e.g., a pre-evacuated vacuum chamber); for instance, in one embodiment, the device may be applied to the skin and activated in some fashion to create and/or access the vacuum source. In yet another example, a chemical reaction may be used to create a vacuum, e.g., a reaction in which a gas is produced, which can be harnessed to provide the mechanical force to create a vacuum. In still another example, a component of the device may be able to create a vacuum in the absence of mechanical force. In another example, the device may include a self-contained vacuum actuator, for example, chemical reactants, a deformable structure, a spring, a piston, etc.

In one set of embodiments, the device may be able to create a pressure differential (e.g. a vacuum). The pressure differential may be created by a pressure regulator. As used here, "pressure regulator" is a pressure controller component or system able to create a pressure differential between two or more locations. The pressure differential should be at least sufficient to urge the movement of fluid or other material in accordance with various embodiments of the invention as discussed herein, and the absolute pressures at the two or more locations are not important so long as their differential is appropriate, and their absolute values are reasonable for the purposes discussed herein. For example, the pressure regulator may produce a pressure higher than atmospheric pressure in one location, relative to a lower pressure at another location (atmospheric pressure or some other pressure), where the differential between the pressures is sufficient to urge fluid in accordance with the invention. In another example, the regulator or controller will involve a pressure lower than atmospheric pressure (a vacuum) in one location, and a higher pressure at another location(s) (atmospheric pressure or a different pressure) where the differential between the pressures is sufficient to urge fluid in accordance with the invention. Wherever "vacuum" or "pressure" is used herein, in association with a pressure regulator or pressure differential of the invention, it should be understood that the opposite can be implemented as well, as would be understood by those of ordinary skill in the art, i.e., a vacuum chamber can be replaced in many instances with a pressure chamber, for creating a pressure differential suitable for urging the movement of fluid or other material.

The pressure regulator may be an external source of vacuum (e.g. a lab, clinic, hospital, etc., house vacuum line or external vacuum pump), a mechanical device, a vacuum chamber, pre-packaged vacuum chamber, or the like. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like. Vacuum chambers can be used in some embodiments, where the device contains, e.g., regions in which a vacuum exits or can be created (e.g. a variable volume chamber, a change in volume of which will affect vacuum or pressure). A vacuum chamber can include pre-evacuated (i.e., pre-packaged) chambers or regions, and/or self-contained actuators.

A "self-contained" vacuum (or pressure) regulator means one that is associated with (e.g., on or within) the device, e.g. one that defines an integral part of the device, or is a separate component constructed and arranged to be specifically connectable to the particular device to form a pressure differential (i.e., not a connection to an external source of vacuum such as a hospital's, clinic's, or lab's house vacuum line, or a vacuum pump suitable for very general use). In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

One category of self-contained vacuum or pressure regulators of the invention includes self-contained assisted regulators. These are regulators that, upon actuation (e.g., the push of a button, or automatic actuation upon, e.g., removal from a package or urging a device against the skin), a vacuum or pressure associated with the device is formed where the force that pressurizes or evacuates a chamber is not the same as the actuation force. Examples of self-contained assisted regulators include chambers evacuated by expansion driven by a spring triggered by actuation, release of a shape-memory material or expandable material upon actuation, initiation of a chemical reaction upon actuation, or the like.

Another category of self-contained vacuum or pressure regulators of the invention are devices that are not necessarily pre-packaged with pressure or vacuum, but which can be pressurized or evacuated, e.g. by a subject, health care professional at a hospital or clinic prior to use, e.g. by connecting a chamber of the device to a source of vacuum or pressure. For example, the subject, or another person, may actuate the device to create a pressure or vacuum within the device, for example, immediately prior to use of the device.

The vacuum or pressure regulator may be a "pre-packaged" pressure or vacuum chamber in the device when used (i.e., the device can be provided ready for use by a subject or practitioner with an evacuated region on or in the device, without the need for any actuation to form the initial vacuum). A pre-packaged pressure or vacuum chamber regulator can, e.g., be a region evacuated (relative to atmospheric pressure) upon manufacture and/or at some point prior to the point at which it is used by a subject or practitioner. For example, a chamber is evacuated upon manufacture, or after manufacture but before delivery of the device to the user, e.g. the clinician or subject. For instance, in some embodiments, the device contains a vacuum chamber having a vacuum of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg below atmospheric pressure.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum chambers, where a seal is punctured in some manner to create a vacuum. For instance, upon puncturing the seal, a vacuum chamber may be in fluidic communication with a needle, which can be used to move the skin towards the device, receive fluid from the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone) diol, or compositions of oligo(epsilon-caprolactone)dimethacrylate and n-butyl acrylate.

In yet another example, a chemical reaction may be used to create a vacuum, e.g., a reaction in which a gas is produced, which can be harnessed to provide the mechanical force to create a vacuum. In some embodiments, the device may be used to create a vacuum automatically, once activated, without any external control by a user.

In one set of embodiments, the device contains a vacuum chamber that is also used as a storage chamber to receive blood or other fluid received from the subject into the device. For instance, blood received from a subject through or via the substance transfer component may enter the vacuum chamber due to its negative pressure (i.e., because the chamber has an internal pressure less than atmospheric pressure), and optionally stored in the vacuum chamber for later use. A non-limiting example is illustrated in FIG. 3. In this figure, device 600 contains vacuum chamber 610, which is connected to substance transfer component 620 (which may include, e.g., one or more microneedles). Upon activation of vacuum chamber 610 (e.g., using actuator 660, as discussed below), vacuum chamber 610 may be put into fluidic communication with substance transfer component 620. Substance transfer component 620 may accordingly cause negative pressure to be applied to the skin of the subject, for instance, due to the internal pressure within vacuum chamber 610. Fluid (e.g., blood) exiting the skin via substance transfer component 620 may accordingly be drawn into the device and into vacuum chamber 610, e.g., through conduit 612. The fluid collected by the device can then be analyzed within the device or removed from the device for analysis, storage, etc.

In another set of embodiments, however, the device may include separate vacuum chambers and storage chambers (e.g., chambers to store fluid such as blood from the subject). The vacuum chamber and storage chambers may be in fluid communication, and may have any suitable arrangement. In some embodiments, the vacuum from the vacuum chamber may be used, at least in part, to receive fluid from the skin, which is then directed into a storage chamber, e.g., for later analysis or use, for example, as discussed below. As an example, blood may be received into the device, flowing towards a vacuum chamber, but the fluid may be prevented from entering the vacuum chamber. For instance, in certain embodiments, a material permeable to gas but not to a liquid such as blood may be used. For example, the material may be a membrane such as a hydrophilic or hydrophobic membrane having a suitable porosity, a porous structure, a porous ceramic frit, a dissolvable interface (e.g., formed from a salt or a polymer, etc.), or the like.

In some embodiments, the flow of blood (or other fluid) into the storage chamber may be controlled using a flow controller. The flow controller may be manually and/or automatically controlled to control the flow of blood. The flow controller may activate or deactivate when a certain amount or volume of fluid has entered the storage chamber in certain cases. For instance, the flow controller may stop blood flow after a predetermined amount or volume of blood has entered the storage chamber, and/or the flow controller may be able to control the internal pressure of the storage chamber, e.g., to a specific level, such as a predetermined level. Examples of suitable flow controllers for the device include, but are not limited to, a membrane, a valve, a dissolvable interface, a gate, or the like.

Thus, in some cases, the device may be constructed and arranged to reproducibly obtain from the subject a controlled amount of fluid, e.g., a controlled amount or volume of blood. The amount of fluid reproducibly obtained from the subject may be controlled, for example, using flow controllers, materials permeable to gas but not to liquids, membranes, valves, pumps, gates, microfluidic systems, or the like, as discussed herein. In particular, it should be noted that the volume of blood or other fluid obtained from the subject need not be strictly a function of the initial vacuum pressure or volume within the device. For example, a flow controller may initially be opened (e.g., manually, automatically, electronically, etc.) to allow fluid to begin entering the device; and when a predetermined condition is reached (e.g., when a certain volume or amount of blood has entered the device), the flow controller may be closed at that point, even if some vacuum pressure remains within the device. In some cases, this control of fluid allows the amount of fluid reproducibly obtained from the subject to be controlled to a great extent. For example, in one set of embodiments, the amount of fluid received from the subject may be controlled to be less than about 1 ml, may be less than about 300 microliters, less than about 100 microliters, less than about 30 microliters, less than about 10 microliters, less than about 3 microliters, less than about 1 microliter, etc.

In certain embodiments, the substance transfer component may be fastened on a deployment actuator. In some cases, the deployment actuator can bring the substance transfer component to the skin, and in certain instances, insert the substance transfer component into the skin. For example, the substance transfer component can be moved mechanically, electrically (e.g., with the aid of a servo, which may be computer-controlled), pneumatically, via a piston, a screw, a mechanical linkage, or the like. In one set of embodiments, the deployment actuator can insert the substance transfer component into the skin at a speed of at least about 0.1 cm/s, at least about 0.3 cm/s, about 1 cm/s, at least about 3 cm/s, at least about 10 cm/s, at least about 30 cm/s, at least about 1 m/s, at least about 2 m/s, at least about 3 m/s, at least about 4 m/s, at least about 5 m/s, at least about 6 m/s, at least about 7 m/s, at least about 8 m/s, at least about 9 m/s, at least about 10 m/s, at least about 12 m/s, etc., at the point where the substance transfer component initially contacts the skin. Without wishing to be bound by any theory, it is believed that relatively faster insertion speeds may increase the ability of the substance transfer component to penetrate the skin (without deforming the skin or causing the skin to move in response), and/or decrease the amount of pain felt by the application of the substance transfer component to the skin. Any suitable method of controlling the penetration speed into the skin may be used, include those described herein.

In some embodiments, the device may be an electrical and/or a mechanical device applicable or affixable to the surface of the skin, e.g., using adhesive, or other techniques such as those described herein. The adhesive may be permanent or temporary, and may be used to affix the device to the surface of the skin. The adhesive may be any suitable adhesive, for example, a pressure sensitive adhesive, a contact adhesive, a permanent adhesive, a hydrogel, a cyanoacrylate, a glue, a gum, hot melts, an epoxy, or the like. In some cases, the adhesive is chosen to be biocompatible or hypoallergenic.

In another set of embodiments, the device may be mechanically held to the skin, for example, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

As another example, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

Any or all of the arrangements described herein can be provided proximate a subject, for example on or proximate a subject's skin. Activation of the devices can be carried out in a variety of ways. In one embodiment, a device can be applied to a subject and a region of the device activated (e.g., pushed, pressed, or tapped by a user) to inject a needle or a microneedle so as to access interstitial fluid. The same or a different tapping or pushing action can activate a vacuum source, open and/or close one or more of a variety of valves, or the like. The device can be a simple one in which it is applied to the skin and operates automatically (where e.g., application to the skin accesses interstitial fluid and draws interstitial fluid into an analysis region) or the device can be applied to the skin and one tapping or other activation can cause fluid to flow through administration of a needle or a microneedle, opening of a valve, activation of vacuum, or any combination. Any number of activation protocols can be carried out by a user repeatedly pushing or tapping a location or selectively, sequentially, and/or periodically activating a variety of switches. In another arrangement, activation of needles or microneedles, creation of suction blisters, opening and/or closing of valves, and other techniques to facilitate one or more analysis can be carried out electronically or in other manners facilitated by the subject or by an outside controlling entity. For example, a device or patch can be provided proximate a subject's skin and a radio frequency, electromagnetic, or other signal can be provided by a nearby controller or a distant source to activate any of the needles, blister devices, valves or other components of the devices described so that any assay or assays can be carried out as desired.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles, viscoelastic fluids, and the like. For example, the fluid may include a flowable matrix or a gel, e.g., formed from biodegradable and/or biocompatible material such as polylactic acid, polyglycolic acid, poly(lactic-co-glycolic acid), etc., or other similar materials.

According to one aspect of the invention, the device is of a relatively small size. In some embodiments, the device may be sized such that it is wearable and/or carryable by a subject. For example, the device may be self-contained, needing no wires, cables, tubes, external structural elements, or other external support. The device may be positioned on any suitable position of the subject, for example, on the arm or leg, on the back, on the abdomen, etc. As mentioned, in some embodiments, the device may be affixed or held onto the surface of the skin using any suitable technique, e.g., using adhesives, mechanical elements such as straps, belts, buckles, strings, ties, elastic bands, or the like. In some cases, the device may be positioned on the subject such that the subject is able to move around (e.g., walking, exercising, typing, writing, drinking or eating, using the bathroom, etc.) while wearing the device. For example, the device may have a mass and/or dimensions such that the subject is able to wear the device for at least about 5 minutes, and in some cases for longer periods of time, e.g., at least about 10 minutes, at least about 15 minutes, at least about 30 minutes, at least about 45 minutes, at least about 1 hour, at least about 3 hours, at least 5 hours, at least about 8 hours, at least about 1 day, at least about 2 days, at least about 4 days, at least about 1 week, at least about 2 weeks, at least about 4 weeks, etc.

In certain embodiments, the may also include a device actuator. The device actuator may be constructed and arranged to cause exposure of the substance transfer component to the skin upon actuation of the device actuator. For example, the activator may cause the substance transfer component to release a chemical to contact the skin, a microneedle or other substance transfer component to be driven into the skin, a vacuum to be applied to the skin, a jet of fluid to be directed to the skin, or the like. The device actuator may be actuated by the subject, and/or by another person (e.g., a health care provider), or the device itself may be self-actuating, e.g., upon application to the skin of a subject. The actuator may be actuated once, or multiple times in some cases.

The device may be actuated, for example, by pushing a button, pressing a switch, moving a slider, turning a dial, or the like. The subject, and/or another person, may actuate the actuator. In some cases, the device may be remotely actuated. For example, a health care provider may send an electromagnetic signal which is received by the device in order to activate the device, e.g., a wireless signal, a radio signal, etc.

In one set of embodiments, the device may include channels such as microfluidic channels, which may be used to deliver and/or receive fluids and/or other materials into or out of the skin, e.g., within the pooled region of fluid. In some cases, the microfluidic channels are in fluid communication with a substance transfer component that is used to deliver and/or receive fluids to or from the skin. For example, in one set of embodiments, the device may include a hypodermic needle that can be inserted into the skin, and fluid may be delivered into the skin via the needle and/or received from the skin via the needle. The device may also include one or more microfluidic channels to contain fluid for delivery to the needle, e.g., from a source of fluid, and/or to receive fluid from the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For example, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio, e.g., an aspect ratio (length to average cross-sectional dimension) of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

In some cases, the device may contain one or more chambers or reservoirs for holding fluid. In some cases, the chambers may be in fluidic communication with one or more substance transfer components and/or one or more microfluidic channels. For instance, the device may contain a chamber for collecting fluid received from a subject (e.g., for storage and/or later analysis), a chamber for containing a fluid for delivery to the subject (e.g., blood, saline, optionally containing drugs, hormones, vitamins, pharmaceutical agents, or the like), etc.

After receipt of the fluid into the device, the device, or a portion thereof, may be removed from the skin of the subject, e.g., by the subject or by another person. For example, the entire device may be removed, or a portion of the device containing the storage reservoir may be removed from the device, and optionally replaced with another storage reservoir. Thus, for instance, in one embodiment, the device may contain two or more modules, for example, a first module that is able to cause receiving of fluid from the skin into a storage reservoir, and a second module containing the storage module. In some cases, the module containing the storage reservoir may be removed from the device. Other examples of modules and modular systems are discussed below; other examples are discussed in U.S. patent application Ser. No. 12/915,735, filed Oct. 29, 2010, entitled "Modular Systems for Application to the Skin," published as U.S. Patent Application Publication No. 2011/0105872 on May 5, 2011, incorporated by reference herein in its entirety.

A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science*, 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering*, 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In another aspect, the present invention is directed to a kit including one or more of the compositions previously discussed, e.g., a kit including a device for the delivery and/or receiving of fluid from the skin, a kit including a device able to create a pooled region of fluid within the skin of a subject, a kit including a device able to determine a fluid, or the like. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or subcontractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. Provisional Patent Application Ser. No. 61/480,977, filed Apr. 29, 2011, entitled "Delivering and/or Receiving Fluids," by Gonzales-Zugasti, et al.; U.S. Provisional Pat. Apl. Ser. No. 61/480,941, entitled "Plasma or Serum Production and Removal of Fluids Under Reduced Pressure," filed on Apr. 29, 2011 by Haghgooie, et al.; U.S. Provisional Patent Application Ser. No. 61/480,960, filed Apr. 29, 2011, entitled "Systems and Methods for Collecting Fluid from a Subject," by Haghgooie, et al.; U.S. patent application Ser. No. 12/478,756, filed Jun. 4, 2009, entitled "Compositions and Methods for Diagnostics, Therapies, and Other Applications," by Levinson, published as U.S. Pat. Apl. Pub. No. 2010/0069726 on Mar. 18, 2010; U.S. patent application Ser. No. 12/716,222, filed Mar. 2, 2010, entitled "Oxygen Sensor," by Levinson, et al., published as U.S. Pat. Apl. Pub. No. 2010/0249560 on Sep. 30, 2010; U.S. patent application Ser. No. 12/716,233, filed Mar. 2, 2010, entitled "Systems and Methods for Creating and Using Suction Blisters or Other Pooled Regions of Fluid within the Skin," by Levinson, et al., published as U.S. Pat. Apl. Pub. No. 2011/0009847 on Jan. 13, 2011; U.S. patent application Ser. No. 12/716,226, filed Mar. 2, 2010, entitled "Techniques and Devices Associated with Blood Sampling," by Levinson, et al., published as U.S. Pat. Apl. Pub. No. 2010/0256524 on Oct. 7, 2010; U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al., published as U.S. Pat. Apl. Pub. No. 2010/0256465 on Oct. 7, 2010; U.S. patent application Ser. No. 12/953,744, filed Nov. 24, 2010, entitled "Patient-Enacted Sampling Technique," by Levinson, et al.; U.S. patent application Ser. No. 12/915,735, filed Oct. 29, 2010, entitled "Systems and Methods for Application to Skin and Control of Actuation, Delivery, and/or Perception Thereof," by Chickering, et al.; U.S. patent application Ser. No. 12/915,789, filed Oct. 29, 2010, entitled "Systems and Methods for Treating, Sanitizing, and/or Shielding the Skin or Devices Applied to the Skin," by Bernstein, et al.; U.S. patent application Ser. No. 12/915,820, filed Oct. 29, 2010, entitled "Relatively Small Devices Applied to the Skin, Modular Systems, and Methods of Use Thereof," by Bernstein, et al.; U.S. patent application Ser. No. 13/006,177, filed Jan. 13, 2011, entitled "Rapid Delivery and/or Withdrawal of Fluids," by Chickering, et al.; U.S. patent application Ser. No. 13/006,165, filed Jan. 13, 2011, entitled "Sampling Device Interfaces," by Chickering, et al.; U.S. Prov. Pat. Apl. Ser. No. 61/357,582, filed Jun. 23, 2010, entitled "Sampling Devices and Methods Involving Relatively Little Pain," by Chickering, et al.; U.S. Prov. Pat. Apl. Ser. No. 61/367,607, filed Jul. 26, 2010, entitled "Rapid Delivery and/or Withdrawal of Fluids," by Davis, et al.; U.S. Prov. Pat. Apl. Ser. No. 61/373,764, filed Aug. 13, 2010, entitled "Clinical and/or Consumer Techniques and Devices," by Chickering, et al.; and U.S. Prov. Pat. Apl. Ser. No. 61/411,566, filed Nov. 9, 2010, entitled "Systems and Interfaces for Blood Sampling," by Brancazio, et al. Also incorporated herein by reference in their entireties are an international patent application entitled "Delivering and/or Receiving Fluids," and an international patent application entitled "Methods and Devices for Withdrawing Fluids from a Subject Using Reduced Pressure," each filed on even date herewith. In addition, U.S. Provisional Patent Application Ser. No. 61/480,941, filed Apr. 29, 2011, entitled "Plasma or Serum Production and Removal of Fluids under Reduced Pressure," by Haghgooie, et al., and U.S. Provisional Patent Application Ser. No. 61/549,437, filed Oct. 20, 2011, entitled "Systems and Methods for Collection and/or Manipulation of Blood Spots or Other Bodily Fluids," by Bernstein, et al. are each incorporated herein by reference in its entirety.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    applying, to a subject having skin, a device to the skin of the subject, the device comprising a substance transfer component comprising one or more needles, a substrate comprising paper for absorbing blood, and a pressure controller able to create an internal pressure less than atmospheric pressure within a vacuum chamber within the device;
    causing the device to insert the one or more needles into the skin using a deployment actuator that moves the one or more needles from a first position within the device to a second position within the device where the one or more needles are inserted into the skin, and to apply reduced pressure to the skin of the subject from the vacuum chamber, to withdraw blood from the skin of the subject into the device such that the blood contacts the substrate comprising paper and is absorbed into the paper;
    moving the one or more needles from second position within the device to the first position within the device while the device is applied to the skin without using the deployment actuator;
    drying the absorbed blood in the substrate to form a dried blood spot in the substrate; and
    removing the substrate from the device.

2. The method of claim 1, wherein the substrate comprises filter paper.

3. The method of claim 1, wherein the substrate comprises cotton-based paper.

4. The method of claim 1, wherein the substrate comprises cotton linter paper.

5. The method of claim 1, wherein a portion of the device is sealable to create an airtight portion surrounding the substrate for absorbing blood.

6. The method of claim 5, wherein the device comprises a movable portion that sealingly creates the airtight portion.

7. The method of claim 1, wherein the device comprises a cover for covering at least a portion of the substance transfer component.

8. The method of claim 1, wherein the device further comprises a tracking apparatus.

9. The method of claim 1, wherein the substrate further comprises a stabilizer.

10. The method of claim 9, wherein the stabilizer comprises a chelating agent.

11. The method of claim 9, wherein the stabilizer comprises an enzyme inhibitor.

12. The method of claim 11, wherein the stabilizer comprises a lysing agent.

13. The method of claim 9, wherein the stabilizer is contained within the substrate for absorbing blood.

14. The method of claim 1, wherein drying the absorbed blood in the substrate comprises exposing the substrate to an environment external to the device.

15. The method of claim 1, wherein drying the absorbed blood in the substrate comprises exposing the substrate to an internal environment contained within the device.

16. The method of claim 15, wherein the internal environment contained within the device comprises desiccant.

17. The method of claim 1, wherein at least one of the one or more needles is a microneedle.

18. The method of claim 1, further comprising shipping at least the substrate.

19. The method of claim 18, comprising shipping at least the substrate by mail.

20. The method of claim 18, comprising shipping at least the substrate at ambient temperature.

21. The method of claim 1, comprising causing the device to insert the one or more needles into the skin, and to apply reduced pressure to the skin of the subject, by pressing a button on the device.

22. The method of claim 1, wherein the deployment actuator comprises a spring.

23. The method of claim 1, wherein the deployment actuator can only be actuated once.

24. The method of claim 1, wherein the deployment actuator moves the one or more needles into the skin at a speed of at least about 0.1 cm/s.

25. The method of claim 1, further comprising a microfluidic channel for flowing the blood to the substrate for absorbing blood.

* * * * *

UNITED STATES PATENT AND TRADEMARK OFFICE
CERTIFICATE OF CORRECTION

PATENT NO. : 11,253,179 B2  
APPLICATION NO. : 15/156386  
DATED : February 22, 2022  
INVENTOR(S) : Howard Bernstein et al.

Page 1 of 1

It is certified that error appears in the above-identified patent and that said Letters Patent is hereby corrected as shown below:

In the Claims

Column 40, Lines 27-28, Claim 12 should read:
-- 12. The method of claim 9, wherein the stabilizer comprises a lysing agent. --

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*